United States Patent
Damiani et al.

(10) Patent No.: US 6,258,998 B1
(45) Date of Patent: Jul. 10, 2001

(54) METHOD OF CLONING PORCINE ANIMALS

(75) Inventors: Philip Damiani, Madison; Jeffrey M. Betthauser, Windsor; Erik J. Forsberg, Fitchburg; Michael D. Bishop, Rio, all of WI (US)

(73) Assignee: Infigen, Inc., DeForest, WI (US)

( * ) Notice: Subject to any disclaimer, the term of this patent is extended or adjusted under 35 U.S.C. 154(b) by 0 days.

(21) Appl. No.: 09/199,138

(22) Filed: Nov. 24, 1998

(51) Int. Cl.⁷ ............................ C12N 15/00; A01K 67/00; A01K 67/027
(52) U.S. Cl. .................................... 800/24; 800/8; 800/17
(58) Field of Search ................................... 800/8, 17, 25, 800/24; 435/325

(56) References Cited

U.S. PATENT DOCUMENTS

| | | |
|---|---|---|
| 4,664,097 | 5/1987 | McGrath et al. . |
| 4,994,384 | 2/1991 | Prather et al. . |
| 5,021,244 | 6/1991 | Spaulding . |
| 5,057,420 | 10/1991 | Massey et al. . |
| 5,096,822 | 3/1992 | Rosenkrans et al. . |
| 5,160,312 | 11/1992 | Voekel et al. . |
| 5,213,979 | 5/1993 | First et al. . |
| 5,346,990 | 9/1994 | Spaulding . |
| 5,354,855 | 10/1994 | Cech et al. . |
| 5,439,362 | 8/1995 | Spaulding . |
| 5,453,357 | 9/1995 | Hogan et al. . |
| 5,496,720 | 3/1996 | Susko-Parrish et al. . |
| 5,523,226 * | 6/1996 | Wheeler .............................. 435/240.2 |
| 5,589,582 | 12/1996 | Hawley et al. . |
| 5,591,610 | 1/1997 | Cech et al. . |
| 5,612,205 | 3/1997 | Kay et al. . |
| 5,633,076 | 5/1997 | DeBoer et al. . |
| 5,645,986 | 7/1997 | West et al. . |

FOREIGN PATENT DOCUMENTS

| | | |
|---|---|---|
| 0 264 166 | 9/1997 | (EP) . |
| 93/16729 | 9/1993 | (WO) . |
| 93/22432 | 11/1993 | (WO) . |
| 94/19935 | 9/1994 | (WO) . |
| 94/26884 | 11/1994 | (WO) . |
| 95/10599 | 4/1995 | (WO) . |
| 95/17085 | 6/1995 | (WO) . |
| 95/20042 | 7/1995 | (WO) . |
| 95/28412 | 10/1995 | (WO) . |
| 96/06165 | 2/1996 | (WO) . |
| 96/07732 | 3/1996 | (WO) . |
| 97/07668 | 3/1997 | (WO) . |
| 97/07669 | 3/1997 | (WO) . |
| 97/12035 | 4/1997 | (WO) . |
| 97/37009 | 10/1997 | (WO) . |
| 98/16630 | 4/1998 | (WO) . |

OTHER PUBLICATIONS

Abeydeera et al., "Coculture with Follicular Shell Pieces Can Enhance the Developmental Competence of Pig Oocytes after In Vitro Fertilization: Relevance to Intracellular Glutathione," *Biology of Reproduction* 58:213–218 (1998).

Ashworth et al., "DNA microsatellite analysis of Dolly," *Nature* 394:329 (1998).

Bellow et al., "Embryo Transfer: Application of Transvaginal Ultrasound for Performing Amniocentesis in Cattle," *Theriogenology* 45(1):225 (1996).

Bustad and McLellan, "Miniature Swine: Development, Management, and Utilization," *Laboratory Animal Care* 18(2):280–287 (1968).

Campbell et al., "Sheep cloned by nuclear transfer from a cultured cell line," *Nature* 380:64–66 (1996).

Collas and Barnes, "Nuclear Transplantation by Microinjection of Inner Cell Mass and Granulosa Cell Nuclei," *Molecular Reproduction and Development* 38:264–267 (1994).

Damiani et al., "Evaluation of Developmental Compotence, Nuclear and Ooplasmic Maturation of Calf Oocytes," *Molecular Reproduction and Development* 45:521–534 (1996).

Darling and Morgan, *Animal Cells: Cuture and Media—Essential Data*, John Wiley & Sons, New York, p. 12 (1994).

Delhaise et al., "Nuclear Transplantation using Bovine Primordial Germ Cells from Male Fetuses," *Reprod. Fertil. Dev.* 7:1217–1219 (1995).

Dobrinsky et al., "Development of a Culture Medium (BECM–3) for Porcine Embryos: Effects of Bovine Serum Albumin and Fetal Bovine Serum on Embryo Devlopment," *Biology of Reproduction* 55:1069–1074 (1996).

England et al., "Conceptual and Operational History of the Development of Miniature Swine," in *Swine in Biomedical Research*, edited by Tumbleson, Plenum Press, New York, 1:17–22 (1986).

Evans et al., "Derivation and Preliminary Characterization of Pluripotent Cell Lines From Porcine and Bovine Blastocysts," *Theriogenology* 33(1):125–128 (1990).

Feng et al., "Piglets From Frozen (−20° C) Embryos Were Born in China," *Theriogenology* 35:199 (1991).

Freshney, *Culture of Animal Cells: A Manual of Basic Technique*, 2ⁿᵈ edition, Alan R. Liss, Inc., New York (1987) (Table of Contents Only).

Freshney, *Culture of Animal Cells: A Manual of Basic Technique*, 3ʳᵈ edition, Alan R. Liss, Inc., New York (1994) (Table of Contents Only).

Funahashi and Day, "Effects of the duration of exposure to hormone supplements on cytoplasmic maturation of pig oocytes in vitro," *Journal of Reproduction and Fertility* 98:179–185 (1993).

(List continued on next page.)

*Primary Examiner*—Deborah Crouch
(74) *Attorney, Agent, or Firm*—Foley & Lardner

(57) ABSTRACT

The present invention relates to materials and methods for cloning porcine animals. The invention relates in part to totipotent cells useful for cloning porcine animals, porcine embryos produced from such cells by employing nuclear transfer techniques, and porcine animals that arise from such cells and embryos.

47 Claims, 3 Drawing Sheets

OTHER PUBLICATIONS

Funahashi et al., "Effects of Electrical Stimulation Before or After in Vitro Fertilization on Sperm Penetration and Pronuclear Formation of Pig Oocytes," *Molecular Reproduction and Development* 36:361–367 (1993).

Funahashi et al., "Pronuclear formation and intracellular glutathione content of in vitro–matured porcine oocytes following in vitro fertilisation and/or electrical activation," *Zygote* 3:273–281 (1995).

Funahashi et al., "Synchronization of Meiosis in Porcine Oocytes by Exposure to Dibutyryl Cyclic Adenosine Monophosphate Improves Developmental Competence Following In Vitro Fertilization," *Biology of Reproduction* 57:49–53 (1997).

Garcia and Salaheddine, "Bovine ultrasound–guided transvaginal amniocentesis," *Theriogenology* 47:1003–1008 (1997).

Geyer, "The role of insulator elements in defining domains of gene expression," *Current Opinion in Genetics & Development* 7(2):242–248 (1997).

Gillespie and Timoney, *Hagan and Bruner's Infectious Diseases of Domestic Animals*, 7th edition, Comstock Publishing Associates (1981) (Table of Contents Only).

Gordon, "Chapter 1—Introduction to controlled breeding in pigs, Embryo transfer and associated techniques in pigs," in *Controlled Reproduction in Pigs*, CAB International, Wallingford, U.K., pp. 1–59 (1997).

Gordon, "Chapter 2—The Sow's Oestrous Cycle and Associated Events," *Controlled Reproduction in Pigs*, CAB International, Wallingford, U.K., pp. 60–76 (1997).

Gordon, "Chapter 7—Increasing Litter Size in Pigs," in *Controlled Reproduction in Pigs*, CAB International, Wallingford, U.K., pp. 164–182 (1997).

Grocholova et al., "The Protein Phosphatase Inhibitor Okadaic Acid Inhibits Exit from Metaphase II in Parthenogenetically Activated Pig Oocytes," *The Journal of Experimental Zoology* 277:49–56 (1997).

Hammer et al., "Production of transgenic rabbits, sheep and pigs by microinjection," *Nature* 315:680–683 (1985).

Hochereau–de Reviers et al., "In vitro culture of embryonic disc cells from porcine blastocysts," *Reprod. Nutr. Dev.* 33:475–483 (1993).

Houdebine (editor), *Transgenic Animals: Generation and Use*, Harwood Academic Publishers, Australia (1997) (Table of Contents Only).

Jolliff et al., "Parthenogenic Development of In Vitro–Matured, In Vivo–Cultured Porcine Oocytes beyond Blastocyst," *Biology of Reproduction* 56:544–548 (1997).

Jolliff and Prather, "Parthenogenic Development of In Vitro Matured Porcine Oocytes to Blastocyst," *Biology of Reproduction* 50(Supplement 1):125 at abstract No. 282 (1994).

Kato and Tsunoda, "Chimerism of mouse male fetal germ cells at 15.5 days post coitum after nuclear transfer," *Journal of Reproduction and Fertility*, Annual Conference of the Society for the Study of Fertility, Abstract Series No. 13, p. 38–39 (Jul. 1994).

Kojima et al., "Embryo transfer," in *Manual of Pig Embryo Transfer Procedures*, National Livestock Breeding Center, Japanese Society for Development of Swine Technology, pp 76–79 pp 7–21 (1998).

Lavoir et al., "Isolation and Identification of Germ Cells From Fetal Bovine Ovaries," *Molecular Reproduction and Development* 37:413–424 (1994).

Leibo and Rall, "Prenatal Diagnosis of Sex in Bovine Fetuses by Amniocentesis," *Theriogenology* 33(2):531–552 (1990).

Long et al., "Morphology and subsequent development in culture of bovine oocytes matured in vitro under various conditions of fertilization," *Journal of Reproduction and Fertility* 102:361–369 (1994).

Machaty et al., "Activation of Porcine Oocytes Via an Exogenously Introduced Rat Muscarinic M1 Receptor," *Biology of Reproduction* 57:85–91 (1997).

Machaty et al., "Parthenogenetic Activation of Porcine Oocytes with Guanosine–5'–0–(3'–thiotriphosphate)," *Biology of Reproduction* 52:753–758 (1995).

Matsui et al., "Derivation of Pluripotential Embryonic Stem Cells from Murine Primordial Germ Cells in Nature," *Cell* 70:841–847 (1992).

Matsui et al., "Effect of Steel factor and leukaemia inhibitory factor on murine primordial germ cells in culture," *Nature* 353:750–752 (1991).

Mattioli et al., "Changes in Maturation–Promoting Activity in the Cytoplasm of Pig Oocytes Throughout Maturation," *Molecular Reproduction and Development* 30:119–125 (1991).

Mattioli et al., "Developmental Competence of Pig Oocytes Matured and Fertlized In Vitro," *Theriogenology* 31(6):1201–1207 (1989).

McGrath et al., "Nuclear Transplantation in the Mouse Embryo by Microsurgery and Cell Fusion," *Science* 220:1300–1302 (1983).

Miller et al., "Expression of human bovine growth hormone gene with a mouse metallothionein–l promoter in transgenic swine alters the secretion of porcine growth hormone and insulin–like growth factor–I," *Journal of Endocrinology* 120:481–488 (1989).

Moore and Piedrahita, "Effects of Heterologous Hematopoietic Cytokines on In Vitro Differentiation of Cultured Porcine Inner Cell Masses," *Molecular Reproduction and Development* 45:139–144 (1996).

Moore and Piedhrahita, "The Effects of Human Leukemia Inhibitory Factor (HLIF) and Culture Medium on In Vitro Differentiation of Cultured Porcine Inner Cell Mass (PICM)," *In Vitro Cell. Dev. Biol.—Animal* 33:62–71 (1997).

Nagashima et al., "Nuclear Transfer of Porcine Embryos Using Cryopreserved Delipated Blastomeres as Donor Nuclei," *Molecular Reproduction and Development* 48:339–343 (1997).

Nagashima et al., "Transplantation of Porcine Blastomere Nuclei into Oocytes Collected from Prepubertal Gilts," *Journal of Reproduction and Development* 38:73–78 (1992).

Nagashima et al., "Changes in Freezing Tolerance of Pig Blastocysts in Peri–Hatching Stage," *Japanese J. Anim. Reprod.* 35:130–134 (1989).

Nussbaum and Prather, "Differential Effects of Protein Synthesis Inhibitors on Porcine Oocyte Activation," *Molecular Reproduction and Development* 41:70–75 (1995).

Petters and Wells, "Culture of pig embryos," *Journal of Reproduction and Fertility*—Supplement 48:61–73 (1993).

Piedrahita et al., "Advances in the generation of transgenic pigs via embryo–derived and primordial germ cell–derived cells," *Journal of Reproduction and Fertility Supplement* 52:245–254 (1997).

Piedrahita et al., "Generation of Transgenic Porcine Chimeras Using Primordial Germ Cell–Derived Colonies," *Biology of Reproduction* 58:1321–1329 (1998).

Piedrahita et al., "On the Isolation of Embryonic Stem Cells: :Comparative Behavior of Murine, Porcine, and Ovine Embryos," *Theriogenology* 34(5):879–901 (1990).

Polge and Day, "Embryo transplantation and preservation," *Control of Pig Reproduction*, edited by Cole and Foxcroft, Butterworths, London, UK, pp. 227–291 (1997).

Prather et al., "Artificial Activation of Porcine Oocytes Matured In Vitro," *Molecular Reproduction and Development* 28:405–409 (1991).

Prather et al., "Nuclear Transplantation in Early Pig Embryos," *Biology of Reproduction* 41:414–418 (1989).

Prather et al., "Nuclear Transplantation in the Pig Embryo: Nuclear Swelling," *Journal of Experimental Zoology* 255:355–358 (1990).

Prochazka et al., "Development of pronuclei in pig oocytes activated by a single electric pulse," *J. Reprod. Fert.* 96:725–734 (1992).

Reed et al., "In Vitro Culture of Pig Embryos," *Theriogenology* 37(1):95–109 (1992).

Resnick et al., "Long–term proliferation of mouse primordial germ cells in culture," *Nature* 359:550–551 (1992).

Rose–Hellekant et al., "Roles of Protein Kinase A and C in Spontaneous Maturation and in Forskolin or 3–Isobutyl–1–Methylaxanthine Maintained Meiotic Arrest of Bovine Oocytes," *Molecular Reproduction and Development* 44:241–249 (1996).

Saito et al., "Ability of porcine blastomere nucleic derived from 8– to 16–cell stage embryos to support development following transfer to enucleated oocytes in vitro," *Assisted Reproductive Technology/Andrology* 3:257–266 (1992).

Sambrook et al., *Molecular Cloning*, 2$^{nd}$ edition, Cold Spring Harbor Laboratory Press (1989) Table of Contents Only).

Sawai et al., "Stage–Specific Requirement of Cysteine during In Vitro Maturation of Porcine Oocytes for Glutathione Associated with Male Pronuclear Formation," *Biology of Reproduction* 57:1–6 (1997).

Schoenbeck et al., "Diacylglycerol–Enhanced Electrical Activation of Porcine Oocytes Matured in Vitro," *Theriogenology* 40:257–266 (1993).

Shim et al., "Isolation of Pluripotent Stem Cells From Cultured Porcine Primordial Germ Cells," *Theriogenology* 47(1):245 (1997).

Shim et al., *Biology of Reproduction*, "Isolation of Pluripotent Stem Cells From Cultured Porcine Primordial Germ Cells," 57:1089–1095 (1997).

Signer et al., "DNA fingerprinting Dolly," *Nature* 394:329–330 (1998).

Sims et al., "Production of Fetuses from Totipotent Cultured Bovine Inner Cell Mass Cells," *Theriogenology* 39:313 (1993).

Spector et al. (eds), *Cells: A Laboratory Manual*, vol. 1, Cold Spring Harbor Laboratory Press (1998) (Table of Contents Only).

Stice et al., "Multiple Generational Bovine Embryo Cloning," *Biology of Reproduction* 48:715–719 (1993).

Strelchenko, "Bovine Pluripotent Stem Cells," *Theriogenology* 45:131–140 (1996).

Strojek et al., "A Method of Cultivating Morphologically Undifferentiated Embryonic Stem Cells from Porcine Blastocysts," *Theriogenology* 33(4):901–913 (1990).

Terlouw et al., "In Vitro Development of Nuclear Transplant Pig Embryos," *Theriogenology* 37(1):309 (1992).

Vos et al., "Bovine fetal fluid collection: transvaginal, ultrasound guided puncture technique," *Veterinary Record* 127:502–504 (1990).

Wagoner et al., "Functional Enucleation of Bovine Oocytes: Effects of Centrifugation and Ultraviolet Light," *Theriogenology* 46:279–284 (1996).

Wakayama et al., "Full–term development of mice from enucleated oocytes injected with cumulus cell nuclei," *Nature* 394:369–374 (1998).

Wang et al., "Quantified Analysis of Cortical Granule Distribution and Exocytosis of Porcine Oocytes during Meiotic Maturation and Activation," *Biology of Reproduction* 56:1376–1382 (1997).

Wheeler, "Development and Validation of Swine Embyonic Stem Cells: a Review," *Reprod. Fertil. Dev.* 6:563–568 (1994).

Wianny et al., "Proliferation and Differentiation of Porcine Inner Cell Mass and Epiblast In Vitro," *Biology and Reproduction* 57:756–764 (1997).

Willadsen, "Nuclear Transplantation in Sheep Embryos," *Nature* 320:63–65 (1986).

Williams, et al., "In Vitro Development of Zygotes from Prepubertal Gilts After Microinjection of DNA," *J. Animal Science* 70:2207–2211 (1992).

Wilmut et al., "Viable offspring derived from fetal and adult mammalian cells," *Nature* 385:810–813 (1997).

Yang et al., "Micromanipulation of Mammalian Embryos: Principles, Progress and Future Possibilities," *Theriogenology* 38:315–335 (1992).

Young et al., "Production of Biopharmaceutical Proteins in the Milk of Transgenic Dairy Animals," *BioPharm* 10(6):34–38 (1997).

Verlander et al (1992) Proceed. Natl. Acad. Sci. 89, 12003–12007.*

Lavitrano et al (1997) Transplantation Proceed. 29, 3508–3509.*

Kroshus et al (1997) J. Heart Lung Transplant. 16, p. 111.*

Onishi, et al., "Pig Cloning by Microinjection of Fetal Fibroblast Nuclei," *Science* 289:1188–1190 (Aug. 18, 2000).

Pennisi, et al., "Perserverance Leads to Cloned Pig in Japan," *Science* 289:1118–1119 (Aug. 18, 2000).

Polejaeva, et al., "Cloned pigs produced by nuclear transfer from adult somatic cells," *Nature* 407:86–90 (Sep. 7, 2000).

Betthauser et al. Production of Cloned Pigs from In Vitro Systems, Nature Biotechnology, Oct. 2000, vol. 15, pp. 1054–1059.*

* cited by examiner

US 6,258,998 B1

METHOD OF CLONING PORCINE ANIMALS

FIELD OF THE INVENTION

The invention relates to the cloning of porcine animals.

BACKGROUND OF THE INVENTION

The following discussion of the background of the invention is merely provided to aid the reader in understanding the invention and is not admitted to describe or constitute prior art to the present invention.

Researchers have been developing methods for cloning mammalian animals over the past two decades. Some reported methods include the steps of (1) isolating a cell, most often an embryonic cell; (2) inserting that cell or a nucleus isolated from the cell into an enucleated oocyte (e.g., the nucleus of the oocyte was previously extracted), and (3) allowing the embryo to mature in vivo.

The first successful nuclear transfer experiment using mammalian cells was reported in 1983, where pronuclei isolated from a murine (mouse) zygote were inserted into an enucleated oocyte and resulted in live offspring(s). McGrath & Solter, 1983, *Science* 220:1300–1302. Subsequently, others described the production of chimeric murine embryos (e.g., embryos that contain a subset of cells having significantly different nuclear DNA from other cells in the embryo) using murine primordial germ cells (PGCs). These cells are and can give rise to pluripotent cells. Matsui et al., 1992, *Cell* 70:841–847 and Resnick et al., 1992, *Nature* 359:550; Kato et al., 1994, *Journal of Reproduction and Fertility* Abstract Series, Society For the Study of Fertility, Annual Conference, Southampton, 13:38. In 1998, researchers reported that murine cumulus cells can be used as nuclear donors in cloning techniques for establishing cloned murine animals. Wakayama et al., 1998, *Nature* 394: 369–374.

Another nuclear transfer experiment was reported in 1986, where an ovine (sheep) embryonic cell was used as a nuclear donor in a cloning process that resulted in a cloned lamb. Willadsen, 1986, *Nature* 320:63–65. More recently, other lambs were reported to be cloned from ovine embryonic cells; serum deprived somatic cells; cells isolated from embryonic discs; and somatic mammary tissue. Campbell et al., 1996, *Nature* 380:64–66; PCT Publication WO 95/20042; Wilmut et al., 1997, *Nature* 385:810–813; and PCT Publications WO 96/07732 and WO 97/07669. Other approaches for cloning ovine animals involved manipulating the activation state of an in vivo matured oocyte after nuclear transfer. PCT Publication WO 97/07668. Publications that disclose cloned lambs report a cloning efficiency that is, at best, approximately 0.4%. Cloning efficiency, as calculated for the previous estimate, is a ratio equal to the number of cloned lambs divided by the number of nuclear transfers used to produce that number of cloned lambs.

Yet another nuclear transfer experiment resulted in a cloned bovine animal (cattle), where the animal was cloned using an embryonic cell derived from a 2–64 cell embryo as a nuclear donor. This bovine animal was reportedly cloned by utilizing nuclear transfer techniques set forth in U.S. Pat. No. 4,994,384 and 5,057,420. Others reported that cloned bovine embryos were formed where an inner cell mass cell of a blastocyst stage embryo was utilized as a nuclear donor in a nuclear transfer procedure. Sims & First, 1993, *Theriogenology* 39:313 and Keefer et al., 1994, *Mol. Reprod. Dev.* 38:264–268. In addition, another publication reported that cloned bovine embryos were prepared by nuclear transfer techniques that utilized a PGC isolated from fetal tissue as a nuclear donor. Delhaise et al., 1995, *Reprod. Fert. Develop.* 7:1217–1219; Lavoir 1994, *J. Reprod Dev.* 37:413–424; and PCT application WO 95/10599 entitled "Embryonic Stem Cell-Like Cells."

With regard to porcine animals (swine), researchers have reported methods for obtaining chimeric animals, specifically, where a nuclear donor is placed inside an enucleated embryonic cell. Prather et al., 1989, *Biology of Reproduction* 41: 414–418; Piedrahita et al., 1998, *Biology of Reproduction* 58: 1321–1329; and WO 94/26884, "Embryonic Stem Cells for Making Chimeric and Transgenic Ungulates," Wheeler, published Nov. 24, 1994.

Also, researchers have reported nuclear transfer experiments for porcine nuclear donors and porcine oocytes. See., e.g., Nagashima et al., 1997, *Mol. Reprod. Dev.* 48: 339–343; Nagashima et al., 1992, J. Reprod. Dev. 38: 73–78; Prather et al., 1989, *Biol. Reprod.* 41: 414–419; Prather et al., 1990, *Exp. Zool.* 255: 355–358; Saito et al., 1992, *Assis. Reprod. Tech. Andro.* 259: 257–266; and Terlouw et al., 1992, *Theriogenology* 37: 309.

In addition, researchers have reported methods for activating porcine oocytes. Grocholová et al., 1997, *J. Exp. Zoology* 277: 49–56; Schoenbeck et al., 1993, *Theriogenology* 40: 257–266; Prather et al., 1991, *Molecular Reproduction and Development* 28: 405–409; Jolliff & Prather, 1997, *Biol. Reprod.* 56: 544–548; Mattioli et al., 1991, *Molecular Reproduction and Development* 30: 109–125; Terlouw et al., 1992, *Theriogenology* 37. 309; Prochazka et al., 1992, *J. Reprod. Fert.* 96: 725–734; Funahashi et al., 1993, *Molecular Reproduction and Development* 36: 361–367; Prather et al., *Bio. Rep. Vol.* 50 Sup 1. 282; Nussbaum et al., 1995, *Molecular Reproduction and Development* 41: 70–75; Funahashi et al., 1995, *Zygote* 3: 273–281; Wang et al., 1997, *Biology of Reproduction* 56: 1376–1382; Piedrahita et al., 1989, *Biology of Reproduction* 58: 1321–1329; Macháty et al., 1997, *Biology of Reproduction* 57: 85–91; and Macháty et al., 1995, *Biology of Reproduction* 52: 753–758.

There remains a long felt need for materials and methods that yield efficient nuclear transfer using a porcine nuclear donor. This long felt need is based in part upon a potential medical application, known as xenotransplantation, which includes procedures for extracting organs from porcine animals and transplanting these organs into humans in need of such organs. U.S. Pat. No. 5,589,582, Hawley et al., issued Dec. 31, 1991; PCT application WO 95/28412, Baetsher et al., published Oct. 26, 1995; PCT application WO 96/06165, Sachs et al., published Feb. 29, 1996; PCT application WO 93/16729, Bazin, published Sep. 2, 1993; PCT application WO 97/12035, Diamond et al., published Apr. 3, 1997; PCT application WO 98/16630, Piedrahita & Bazer, published Apr. 23, 1998.

SUMMARY

The invention relates in part to cloning technologies for porcine animals. The invention also relates in part to totipotent cells and cells that can be made totipotent, for use in cloning procedures and production of porcine animals, embryos produced from these porcine cells using nuclear transfer techniques, porcine animals that arise from these cells and embryos, and methods and processes for establishing such cells, embryos, and animals.

The present invention provides multiple advantages over tools and methods currently utilized for porcine cloning. Such features and advantages include:

(1) Production of cloned porcine animals from virtually any type of cell. The invention provides materials and methods for reprogramming non-totipotent porcine cells into totipotent porcine cells. These non-totipotent porcine cells may be of nonembryonic origin. This feature of the invention allows for an ability to assess a phenotype of an existing porcine animal and then readily establish a totipotent cell line for cloning that animal.

(2) Establishment of totipotent porcine cell lines from virtually any type of porcine cell. In one aspect of the invention, non-totipotent porcine precursor cells can be reprogrammed into totipotent cells. These non-totipotent precursor cells may be non-embryonic cells. Established totipotent porcine cell lines provide an advantage of enhancing cloning efficiency due to lower cellular heterogeneity within cell lines (e.g., cell lines often exhibit lower rates of differentiation than primary cells). In addition, the totipotent cell lines can be manipulated in vitro to produce porcine cells, embryos, and animals whose genomes have been manipulated (e.g., transgenic). Furthermore, totipotent cell lines can be more easily stored, transported, and re-established in culture than other types of cell lines.

(3) Efficiency enhancement for cloning embryos as a result of utilizing asynchronous and karyotypically stable porcine cell lines in a complete in vitro embryo production system.

Cloning efficiency can be expressed by the ratio between the number of embryos resulting from nuclear transfer and the number of nuclear transfers performed to give rise to the embryos. Alternatively, cloning efficiency can be expressed as the ratio between the number of live born animals and the number of nuclear transfers performed to give rise to these animals.

Cultured Cells of the Invention

In a first aspect, the invention features a totipotent porcine cell.

The term "porcine" as used herein can refer to any animal of the family Suidae. A porcine animal can refer to swine of any sort, including, but not limited to, wild boar, domestic swine, miniswine, warthog, peccary, and barboosa. For examples of miniswine, see, e.g., Bustad & McClellan, 1968, *Lab. Anim. Care.* 18: 280–287 and England & Panepinto, 1986, "Conceptual and operational history of the development of miniature swine," *Swine in Biomedical Research* (M. E. Tubleson, ed.), Plenum Press, N Y pp 17–22, each of which is incorporated herein by reference in its entirety, including all figures, tables, and drawings.

The term "totipotent" as used herein can refer to a cell that gives rise to a live born animal. The term "totipotent" can also refer to a cell that gives rise to all of the cells in a particular animal. A totipotent cell can give rise to all of the cells of an animal when it is utilized in a procedure for developing an embryo from one or more nuclear transfer steps. Totipotent cells may also be used to generate incomplete animals such as those useful for organ harvesting, e.g., having genetic modifications to eliminate growth of an organ or appendage by manipulation of a homeotic gene.

The term "live born" as used herein preferably refers to an animal that exists ex utero. A "live born" animal may be an animal that is alive for at least one second from the time it exits the maternal host. A "live born" animal may not require the circulatory system of an in utero environment for survival. A "live born" animal may be an ambulatory animal. Such animals can include pre- and post-pubertal animals. As discussed previously, a live born animal may lack a portion of what exists in a normal animal of its kind.

In preferred embodiments, totipotent cells are (1) cultured; (2) are cultured as cell lines; and are (3) cultured as permanent cell lines.

The term "cultured" as used herein in reference to cells can refer to one or more cells that are undergoing cell division or not undergoing cell division in an in vitro environment. An in vitro environment can be any medium known in the art that is suitable for maintaining cells in vitro, such as suitable liquid media or agar, for example. Specific examples of suitable in vitro environments for cell cultures are described in *Culture of Animal Cells: a manual of basic techniques* ($3^{rd}$ edition), 1994, R. I. Freshney (ed.), Wiley-Liss, Inc.; *Cells: a laboratory manual* (vol. 1), 1998, D. L. Spector, R. D. Goldman, L. A. Leinwand (eds.), Cold Spring Harbor Laboratory Press; and *Animal Cells: culture and media*, 1994, D. C. Darling, S. J. MorganJohn Wiley and Sons, Ltd., each of which is incorporated herein by reference in its entirety including all figures, tables, and drawings. Cells may be cultured in suspension and/or in monolayers with one or more substantially similar cells. Cells may be cultured in suspension and/or in monolayers with a heterogeneous population of cells. The term "heterogeneous" as utilized in the previous sentence can relate to any cell characteristics, such as cell type and cell cycle stage, for example. Cells may be cultured in suspension, cultured as monolayers attached to a solid support, and/or cultured on a layer of feeder cells, for example. The term "feeder cells" is defined hereafter. Furthermore, cells may be successfully cultured by plating the cells in conditions where they lack cell to cell contact. Preferably, cultured cells undergo cell division and are cultured for at least 5 days, more preferably for at least 10 days or 20 days, and most preferably for at least 30 days. Preferably, a significant number of cultured cells do not terminate while in culture. The terms "terminate" and "significant number are defined" hereafter. Nearly any type of cell can be placed in cell culture conditions. Cultured cells can be utilized to establish a cell line.

The term "cell line" as used herein can refer to cultured cells that can be passaged at least one time without terminating. The invention relates to cell lines that can be passaged at least 1, 2, 5, 10, 15, 20, 30, 40, 50, 60, 80, 100, and 200 times. Cell passaging is defined hereafter.

The term "terminating" and "terminate" as used herein with regard to cultured cells may refer to cells that undergo cell death, which can be measured using multiple techniques known to those skilled in the art (e.g., CytoTox96® Cytotoxicity Assay, Promega, Inc. catalog no. G1780; Celltiter96® Aqueous Cell Proliferation Assay Kit, Promega, Inc. catalog no. G3580; and Trypan Blue solution for cytotoxicity assays, Sigma catalog no. T6146). Termination may also be a result of apoptosis, which can be measured using multiple techniques known to persons skilled in the art (e.g., Dead End™ Apoptosis Detection Kit, Promega, Inc. catalog no. G7130). Terminated cells may be identified as those that have undergone cell death and/or apoptosis and have released from a solid surface in culture. In addition, terminated cells may lack intact membranes which can be identified by procedures described above. Also, terminated cells may exhibit decreased metabolic activity, which may be caused in part by decreased mitochondrial activity that can be identified by rhodamine 1,2,3, for example. Furthermore, termination can be refer to cell cultures where a significant number of cultured cells terminate. The term "significant number" in the preceding sentence can refer to about 80% of the cells in culture, preferably about 90% of the cells in culture, more preferably about 100% of the cells in culture, and most preferably 100% of the cells in culture.

The term "suspension" as used herein can refer to cell culture conditions in which cells are not attached to a solid support. Cells proliferating in suspension can be stirred while proliferating using apparatus well known to those skilled in the art.

The term "monolayer" as used herein can refer to cells that are attached to a solid support while proliferating in suitable culture conditions. A small portion of cells proliferating in a monolayer under suitable growth conditions may be attached to cells in the monolayer but not to the solid support. Preferably less than 15% of these cells are not attached to the solid support, more preferably less than 10% of these cells are not attached to the solid support, and most preferably less than 5% of these cells are not attached to the solid support.

The term "substantially similar" as used herein in reference to porcine cells can refer to cells from the same organism and the same tissue. The term "substantially similar" can also refer to cell populations that have not significantly differentiated. For example, preferably less than 15% of the cells in a population of cells have differentiated, more preferably less than 10% of the cell population have differentiated, and most preferably less than 5% of the cell population have differentiated.

The term "plated" or "plating" as used herein in reference to cells can refer to establishing cell cultures in vitro. For example, cells can be diluted in cell culture media and then added to a cell culture plate, dish, or flask. Cell culture plates are commonly known to a person of ordinary skill in the art. Cells may be plated at a variety of concentrations and/or cell densities.

The term "cell plating" can also extend to the term "cell passaging." Cells of the invention can be passaged using cell culture techniques well known to those skilled in the art. The term "cell passaging" can refer to a technique that involves the steps of (1) releasing cells from a solid support or substrate and disassociation of these cells, and (2) diluting the cells in media suitable for further cell proliferation. Cell passaging may also refer to removing a portion of liquid medium containing cultured cells and adding liquid medium to the original culture vessel to dilute the cells and allow further cell proliferation. In addition, cells may also be added to a new culture vessel which has been supplemented with medium suitable for further cell proliferation.

The term "proliferation" as used herein in reference to cells can refer to a group of cells that can increase in number over a period of time.

The term "confluence" as used herein can refer to a group of cells where a large percentage of cells are physically contacted with at least one other cell in that group. Confluence may also be defined as a group of cells that grow to a maximum cell density in the conditions provided. For example, if a group of cells can proliferate in a monolayer and they are placed in a culture vessel in a suitable growth medium, they are confluent when the monolayer has spread across a significant surface area of the culture vessel. The surface area covered by the cells preferably represents about 50% of the total surface area, more preferably represents about 70% of the total surface area, and most preferably represents about 90% of the total surface area.

The term "permanent" or "immortalized" as used herein in reference to porcine cells can refer to cells that may undergo cell division and double in cell numbers while cultured in an in vitro environment a multiple number of times until the cells terminate. A permanent cell line may double over 10 times before a significant number of cells terminate in culture. Preferably, a permanent cell line may double over 20 times or over 30 times before a significant number of cells terminate in culture. More preferably, a permanent cell line may double over 40 times or 50 times before a significant number of cells terminate in culture. Most preferably, a permanent cell line may double over 60 times before a significant number of cells terminate in culture. The term "terminate" is described previously. Cell doubling can be measured by counting the number of cells in culture using techniques well known to a person of ordinary skill in the art. As a measure of cell culture permanence, a number of doublings can be measured until a significant number of cells terminate in culture. The term "significant number" is also described previously.

Permanent cells may be distinguished from non-permanent cells on the basis that permanent cells can be passaged at densities lower than those of non-permanent cells. Specifically, permanent cells can be grown to confluence (described hereafter) when plating conditions do not allow physical contact between the cells. Hence, permanent cells can be distinguished from non-permanent cells when cells are plated at cell densities where the cells do not physically contact one another.

In preferred embodiments, (1) totipotent cells are not alkaline phosphatase positive (e.g., cells do not appreciably stain for alkaline phosphatase); (2) totipotent cells arise from at least one precursor cell; (3) a precursor cell is isolated from and/or arises from any region of a porcine animal; (4) a precursor cell is isolated from and/or arises from any cell in culture; (5) a precursor cell is selected from the group consisting of a non-embryonic cell, a non-fetal cell, a differentiated cell, an undifferentiated cell, a somatic cell, an embryonic cell, a fetal cell, an embryonic stem cell, a primordial germ cell, a genital ridge cell, a cumulus cell, an amniotic cell, a fetal fibroblast cell, a hepatacyte, an embryonic germ cell, an adult cell, a cell isolated from an asynchronous population of cells, and a cell isolated from a synchronized population of cells where the synchronous population is not arrested in the $G_0$ stage of the cell cycle; (6) totipotent cells have a morphology of an embryonic germ cell.

The term "alkaline phosphatase positive" as used herein can refer to a detectable presence of cellular alkaline phosphatase. Cells that are not alkaline phosphatase positive do not stain appreciably using a procedure for visualizing cellular alkaline phosphatase. Procedures for detecting the presence of cellular alkaline phosphatase are well-known to a person of ordinary skill in the art. See, e.g., Matsui et al., 1991, "Effect of Steel Factor and Leukemia Inhibitory Factor on Murine Primordial Germ Cells in Culture," *Nature* 353: 750–752. Examples of cells that stain appreciably for alkaline phosphatase can be found in the art. See, e.g., U.S. Pat. No. 5,453,357, Entitled "Pluripotent Embryonic Stem Cells and Methods of Making Same," issued to Hogan on Sep. 26, 1995, which is incorporated by reference herein in its entirety, including all figures, tables, and drawings.

The term "precursor cell" or "precursor cells" as used herein can refer to a cell or cells used to establish cultured porcine cells or a cultured porcine cell line. A precursor cell or cells may be isolated from nearly any cellular entity. For example, a precursor cell or cells may be isolated from blastocysts, embryos, fetuses, and cell lines (e.g., cell lines established from embryonic cells), preferably isolated from fetuses and/or cell lines established from fetal cells, and more preferably isolated from ex utero animals and/or cell cultures and/or cell lines established from such ex utero animals. An ex utero animal may exist as a newborn animal (e.g., 5 days after birth), adolescent animal (e.g., pre-pubescent animal), pubescent animal (e.g., after ovulation or production of viable sperm), and adult animal (e.g., post pubescent). The ex utero animals may be alive or post mortem. Precursor cells may be cultured or non-cultured. Furthermore, precursor cells may be at a time cryopreserved or frozen (e.g., cryopreserved cells may be utilized as precursor cells to establish a cell culture). These examples are not meant to be limiting and a further description of these exemplary precursor cells is provided hereafter.

The term "arises from" as used herein can refer to the conversion of one or more cells into one or more cells having at least one differing characteristic. For example, (1) a non-totipotent precursor cell can be converted into a totipotent cell by utilizing features of the invention described hereafter; (2) a precursor cell can develop a cell morphology of an embryonic germ cell; (3) a precursor cell can give rise to a cultured cell; (4) a precursor cell can give rise to a cultured cell line; and (5) a precursor cell can give rise to a cultured permanent cell line. A conversion process can be referred to as a reprogramming step. In addition, the term "arises from" can refer to establishing totipotent embryos from totipotent cells of the invention by using a nuclear transfer process, as described hereafter.

The term "reprogramming" or "reprogrammed" as used herein can refer to materials and methods that can convert a cell into another cell having at least one differing characteristic. Also, such materials and methods may reprogram or convert a cell into another cell type that is not typically expressed during the life cycle of the former cell. For example, (1) a non-totipotent cell can be reprogrammed into an totipotent cell; (2) a precursor cell can be reprogrammed into a cell having a morphology of an EG cell; and (3) a precursor cell can be reprogrammed into a totipotent cell. An example of materials and methods for converting a precursor cell into a totipotent cell having EG cell morphology is described hereafter.

The term "isolated" as used herein can refer to a cell that is mechanically separated from another group of cells. Examples of a group of cells are a developing cell mass, a cell culture, a cell line, and an animal. These examples are not meant to be limiting and the invention relates to any group of cells. Methods for isolating one or more cells from another group of cells are well known in the art. See, e.g., *Culture of Animal Cells: a manual of basic techniques* ($3^{rd}$ edition), 1994, R. I. Freshney (ed.), Wiley-Liss, Inc.; *Cells: a laboratory manual* (vol. 1), 1998, D. L. Spector, R. D. Goldman, L. A. Leinwand (eds.), Cold Spring Harbor Laboratory Press; and *Animal Cells: culture and media*, 1994, D. C. Darling, S. J. Morgan John Wiley and Sons, Ltd.

The term "non-embryonic cell" as used herein can refer to a cell that is not isolated from an embryo. Non-embryonic cells can be differentiated or nondifferentiated. Non-embryonic cells can refer to nearly any somatic cell, such as cells isolated from an ex utero animal. These examples are not meant to be limiting.

For the purposes of the present invention, the term "embryo" or "embryonic" as used herein can refer to a developing cell mass that has not implanted into an uterine membrane of a maternal host. Hence, the term "embryo" as used herein can refer to a fertilized oocyte, a cybrid (defined herein), a pre-blastocyst stage developing cell mass, and/or any other developing cell mass that is at a stage of development prior to implantation into an uterine membrane of a maternal host. Embryos of the invention may not display a genital ridge. Hence, an "embryonic cell" is isolated from and/or has arisen from an embryo.

An embryo can represent multiple stages of cell development. For example, a one cell embryo can be referred to as a zygote, a solid spherical mass of cells resulting from a cleaved embryo can be referred to as a morula, and an embryo having a blastocoel can be referred to as a blastocyst.

The term "fetus" as used herein can refer to a developing cell mass that has implanted into the uterine membrane of a maternal host. A fetus can include such defining features as a genital ridge, for example. A genital ridge is a feature easily identified by a person of ordinary skill in the art, and is a recognizable feature in fetuses of most animal species. The term "fetal cell" as used herein can refer to any cell isolated from and/or has arisen from a fetus or derived from a fetus, including amniotic cells. The term "non-fetal cell" is a cell that is not derived or isolated from a fetus.

When precursor cells are isolate from a fetus, such precursor cells are preferably isolated from porcine fetuses where the fetus is between 20 days and parturition, between 30 days and 100 days, more preferably between 35 days and 70 days and between 40 days and 60 days, and most preferably about a 55 day fetus. An age of a fetus can be determined by the time that an embryo, which develops into the fetus, is established. For example, a two cell embryo can be referred to as a day one embryo that can develop into a 54 day fetus. The term "about" with respect to fetuses can refer to plus or minus five days.

The term "parturition" as used herein can refer to a time that a fetus is delivered from female recipient. A fetus can be delivered from a female recipient by abortion, c-section, or birth.

The term "primordial germ cell" as used herein can refer to a diploid precursor cell capable of becoming a germ cell. Primordial germ cells can be isolated from any tissue in a developing cell mass, and are preferably isolated from genital ridge cells of a developing cell mass. A genital ridge is a section of a developing cell mass that is well-known to a person of ordinary skill in the art. See, e.g., Strelchenko, 1996, *Theriogenology* 45: 130–141 and Lavoir 1994, *J. Reprod. Dev.* 37: 413–424.

The term "embryonic stem cell" as used herein can refer to pluripotent cells isolated from an embryo that are maintained in in vitro cell culture. Embryonic stem cells may be cultured with or without feeder cells. Embryonic stem cells can be established from embryonic cells isolated from embryos at any stage of development, including blastocyst stage embryos and pre-blastocyst stage embryos. Embryonic stem cells may have a rounded cell morphology and may grow in rounded cell clumps on feeder layers. Embryonic stem cells are well known to a person of ordinary skill in the art. See, e.g., WO 97/37009, entitled "Cultured Inner Cell Mass Cell-Lines Derived from Ungulate Embryos," Stice and Golueke, published Oct. 9, 1997, and Yang & Anderson, 1992, *Theriogenology* 38: 315–335, each of which is incorporated herein by reference in its entirety, including all figures, tables, and drawings. See, e.g., Piedrahita et al., 1998, *Biol. Reprod.* 58: 1321–1329; Wianny et al., 1997, *Biol. Reprod.* 57: 756–764; Moore & Piedrahita, 1997, *In Vitro Cell Biol. Anim.* 33: 62–71; Moore, & Piedrahita, 1996, *Mol. Reprod. Dev.* 45: 139–144; Wheeler, 1994, *Reprod. Fert. Dev.* 6: 563–568; Hochereau-de Reviers & Perreau, *Reprod. Nutr. Dev.* 33: 475–493; Strojek et al., 1990, *Theriogenology* 33: 901–903; Piedrahita et al., 1990, *Theriogenology* 34: 879–901; and Evans et al., 1990, *Theriogenology* 33: 125–129, each of which is incorporated herein by reference in its entirety, including all figures, tables, and drawings.

The term "differentiated cell" as used herein can refer to a precursor cell that has developed from an unspecialized phenotype to a specialized phenotype. For example, embryonic cells can differentiate into an epithelial cell lining the intestine. Materials and methods of the invention can reprogram differentiated cells into totipotent cells. Differentiated cells can be isolated from a fetus or a live born animal, for example.

The term "undifferentiated cell" as used herein can refer to a precursor cell that has an unspecialized phenotype and is capable of differentiating. An example of an undifferentiated cell is a stem cell.

The term "asynchronous population" as used herein can refer to cells that are not arrested at any one stage of the cell cycle. Many cells can progress through the cell cycle and do not arrest at any one stage, while some cells can become arrested at one stage of the cell cycle for a period of time. Some known stages of the cell cycle are $G_1$, S, $G_2$, and M. An asynchronous population of cells is not manipulated to synchronize into any one or predominantly into any one of these phases. Cells can be arrested in the M stage of the cell cycle, for example, by utilizing multiple techniques known in the art, such as by colcemid exposure. Examples of methods for arresting cells in one stage of a cell cycle are discussed in WO 97/07669, entitled "Quiescent Cell Populations for Nuclear Transfer," hereby incorporated herein by reference in its entirety, including all figures, tables, and drawings.

The terms "synchronous population" and "synchronizing" as used herein can refer to a fraction of cells in a population that are within a same stage of the cell cycle. Preferably, about 50% of cells in a population of cells are arrested in one stage of the cell cycle, more preferably about 70% of cells in a population of cells are arrested in one stage of the cell cycle, and most preferably about 90% of cells in a population of cells are arrested in one stage of the cell cycle. Cell cycle stage can be distinguished by relative cell size as well as by a variety of cell markers well known to a person of ordinary skill in the art. For example, cells can be distinguished by such markers by using flow cytometry techniques well known to a person of ordinary skill in the art. Alternatively, cells can be distinguished by size utilizing techniques well known to a person of ordinary skill in the art, such as by the utilization of a light microscope and a micrometer, for example. In a preferred embodiment, cells are synchronized by arresting them (i.e., cells are not dividing) in a discreet stage of the cell cycle.

The terms "embryonic germ cell" and "EG cell" as used herein can refer to a cultured cell that has a distinct flattened morphology and can grow within monolayers in culture. An EG cell may be distinct from a fibroblast cell. This EG cell morphology is to be contrasted with cells that have a spherical morphology and form multicellular clumps on feeder layers. Porcine embryonic germ cells may not require the presence of feeder layers or presence of growth factors in cell culture conditions. Porcine embryonic germ cells may also grow with decreased doubling rates when these cells approach confluence on culture plates. Porcine embryonic germ cells of the invention may be totipotent. Porcine embryonic germ cells of the invention may not appreciably stain for alkaline phosphatase. Preferably, porcine embryonic germ cells are established in culture media that contains a significant concentration of glucose, as described herein.

Porcine embryonic germ cells may be established from a cell culture of nearly any type of porcine precursor cell. Examples of precursor cells are discussed herein, and a preferred precursor cell for establishing a porcine embryonic germ cell culture is a genital ridge cell from a fetus. Genital ridge cells are preferably isolated from porcine fetuses where the fetus is between 20 days and parturition, between 30 days and 100 days, more preferably between 35 days and 70 days and between 40 days and 60 days, and most preferably about a 55 day fetus. An age of a fetus can be determined as described above. The term "about" with respect to fetuses can refer to plus or minus five days. As described herein, EG cells may be physically isolated from a primary culture of cells, and these isolated EG cells may be utilized to establish a cell culture that eventually forms a homogenous or nearly homogenous cell line of EG cells.

The terms "morphology" and "cell morphology" as used herein can refer to form, structure, and physical characteristics of cells. For example, one cell morphology is significant levels of alkaline phosphatase, and this cell morphology can be identified by determining whether a cell stains appreciably for alkaline phosphatase. Another example of a cell morphology is whether a cell is flat or round in appearance when cultured on a surface or in the presence of a layer of feeder cells. Many other cell morphologies are known to a person of ordinary skill in the art and are cell morphologies are readily identifiable using materials and methods well known to those skilled in the art. See, e.g., Culture of Animal Cells: a manual of basic techniques ($3^{rd}$ edition), 1994, R. I. Freshney (ed.), Wiley-Liss, Inc.

The term "cumulus cell" as used herein can refer to any cultured or non-cultured cell that is isolated from cells and/or tissue surrounding an oocyte. Persons skilled in the art can readily identify a cumulus cell. Examples of methods for isolating and culturing cumulus cells are discussed in Damiani et al., 1996, *Mol. Reprod. Dev.* 45: 521–534; Long et al., 1994, *J. Reprod. Fert.* 102: 361–369; and Wakayama et al., 1998, *Nature* 394: 369–373, each of which is incorporated herein by reference in its entireties, including all figures, tables, and drawings.

The term "amniotic cell" as used herein can refer to a cultured or non-cultured cell isolated from amniotic fluid or tissues in contact with amniotic fluid. Persons skilled in the art can readily identify an amniotic cell. Examples of methods for isolating and culturing amniotic cells are discussed in Bellow et al., 1996, *Theriogenology* 45: 225; Garcia & Salaheddine, 1997, *Theriogenology* 47: 1003–1008; Leibo & Rail, 1990, *Theriogenology* 33: 531–552; and Vos et al., 1990, *Vet. Rec.* 127: 502–504, each of which is incorporated herein by reference in its entirety, including all figures tables and drawings.

The term "fetal fibroblast cell" as used herein can refer to any differentiated porcine fetal cell having a fibroblast appearance. Fibroblasts can have a flattened appearance when cultured on culture media plates. Fetal fibroblast cells can also have a spindle-like morphology, density limited for growth, and can have a finite life span in culture of approximately fifty generations. In addition, fetal fibroblast cells may rigidly maintain a diploid chromosomal content and may generate type I collagen. For a description of fibroblast cells, see, e.g., Culture of Animal Cells: a manual of basic techniques ($3^{rd}$ edition), 1994, R. I. Freshney (ed), Wiley-Liss, Inc The term "adult cell" as used herein can refer to any cell isolated from an adult porcine animal. Such an adult cell can be isolated from any part of the porcine animal, including, but not limited to, skin from an ear, skin from an abdominal region, kidney, liver, heart, and lung. Procedures are set forth herein for culturing such adult cells.

In preferred embodiments, (1) totipotent porcine cells of the invention comprise modified nuclear DNA; (2) modified nuclear DNA includes a DNA sequence that encodes a recombinant product; (3) a recombinant product is a polypeptide; (4) a recombinant product is a ribozyme; (4) a recombinant product is expressed in a biological fluid or tissue; (5) a recombinant product confers or partially confers resistance to one or more diseases; (6) a recombinant product confers resistance or partially confers resistance to one or more parasites; (7) a modified nuclear DNA comprises at least one other DNA sequence that can function as a regulatory element; (8) a regulatory element is selected from the group consisting of promoter, enhancer, insulator, and repressor; and (9) a regulatory element is selected from the group consisting of milk protein promoter, urine protein promoter, blood protein promoter, lacrimal duct protein promoter, synovial protein promoter, mandibular gland protein promoter, casein promoter, β-casein promoter, melanocortin promoter, milk serum protein promoter, α-lactalbumin promoter, whey acid protein promoter, uroplakin promoter, α-actin promoter.

The term "modified nuclear DNA" as used herein can refer to a nuclear deoxyribonucleic acid sequence of a cell, embryo, fetus, or animal of the invention that has been manipulated by one or more recombinant DNA techniques. Examples of recombinant DNA techniques are well known to a person of ordinary skill in the art, which can include (1) inserting a DNA sequence from another organism (e.g., a human organism) into target nuclear DNA, (2) deleting one or more DNA sequences from target nuclear DNA, and (3) introducing one or more base mutations (e.g., site-directed mutations) into target nuclear DNA. Cells with modified nuclear DNA can be referred to as "transgenic cells" for the purposes of the invention. Transgenic cells can be useful as materials for nuclear transfer cloning techniques provided herein.

Methods and tools for insertion, deletion, and mutation of nuclear DNA of mammalian cells are well-known to a person of ordinary skill in the art. See, *Molecular Cloning, a Laboratory Manual*, 2nd Ed., 1989, Sambrook, Fritsch, and Maniatis, Cold Spring Harbor Laboratory Press; U.S. Pat. No. 5,633,067, "Method of Producing a Transgenic Bovine or Transgenic Bovine Embryo," DeBoer et al., issued May 27, 1997; U.S. Pat. No. 5,612,205, "Homologous Recombination in Mammalian Cells," Kay et al., issued Mar. 18, 1997; and PCT publication WO 93/22432, "Method for Identifying Transgenic Pre-Implantation Embryos"; WO 98/16630, Piedrahita & Bazer, published Apr. 23, 1998, "Methods for the Generation of Primordial Germ Cells and Transgenic Animal Species," each of which is incorporated herein by reference in its entirety, including all figures, drawings, and tables. These methods include techniques for transfecting cells with foreign DNA fragments and the proper design of the foreign DNA fragments such that they effect insertion, deletion, and/or mutation of the target DNA genome.

Transgenic cells may be obtained in a variety of manners. For example, transgenic cells can be isolated from a transgenic animal. Examples of transgenic porcine animals are well known in the art. Cells isolated from a transgenic animal can be converted into totipotent cells by using the materials and methods provided herein. In another example, transgenic cells can be established from totipotent cells of the invention. Materials and methods for converting non-transgenic cells into transgenic cells are well known in the art, as described previously.

Any of the cell types defined herein can be altered to harbor modified nuclear DNA. For example, embryonic stem cells, embryonic germ cells, fetal cells, and any totipotent cell defined herein can be altered to harbor modified nuclear DNA.

Examples of methods for modifying a target DNA genome by insertion, deletion, and/or mutation are retroviral insertion, artificial chromosome techniques, gene insertion, random insertion with tissue specific promoters, homologous recombination, gene targeting, transposable elements, and/or any other method for introducing foreign DNA. Other modification techniques well known to a person of ordinary skill in the art include deleting DNA sequences from a genome, and/or altering nuclear DNA sequences. Examples of techniques for altering nuclear DNA sequences are site-directed mutagenesis and polymerase chain reaction procedures. Therefore, the invention relates in part to porcine cells that are simultaneously totipotent and transgenic. Such transgenic and totipotent cells can serve as nearly unlimited sources of donor cells for production of cloned transgenic porcine animals.

The term "recombinant product" as used herein can refer to the product produced from a DNA sequence that comprises at least a portion of the modified nuclear DNA. This product can be a peptide, a polypeptide, a protein, an enzyme, an antibody, an antibody fragment, a polypeptide that binds to a regulatory element (a term described hereafter), a structural protein, an RNA molecule, and/or a ribozyme, for example. These products are well defined in the art. This list of products is for illustrative purposes only and the invention relates to other types of products.

The term "ribozyme" as used herein can refer to ribonucleic acid molecules that can cleave other RNA molecules in specific regions. Ribozymes can bind to discrete regions on a RNA molecule, and then specifically cleave a region within that binding region or adjacent to the binding region. Ribozyme techniques can thereby decrease the amount of polypeptide translated from formerly intact message RNA molecules. For specific descriptions of ribozymes, see U.S. Pat. No. 5,354,855, entitled "RNA Ribozyme which Cleaves Substrate RNA without Formation of a Covalent Bond," Cech et al., issued on Oct. 11, 1994, and U.S. Pat. No. 5,591,610, entitled "RNA Ribozyme Polymerases, Dephosphorylases, Restriction Endoribonucleases and Methods," Cech et al., issued on Jan. 7, 1997, each of which is incorporated herein by reference in its entirety including all figures, tables, and drawings.

The terms "biological fluid" or "tissue" as used herein can refer to any fluid or tissue in a biological organism. Fluids may include, but are not limited to, tears, saliva, milk, urine, amniotic fluid, semen, plasma, oviductal fluid, and synovial fluid. Tissues may include, but are not limited to, lung, heart, blood, liver, muscle, brain, pancreas, skin, and others.

The term "confers resistance" as used herein can refer to the ability of a recombinant product to completely abrogate or partially alleviate the symptoms of a disease or parasitic condition. Hence, if a disease is related to inflammation, for example, a recombinant product can confer resistance to that inflammation if inflammation decreases upon expression of the recombinant product. A recombinant product may confer resistance or partially confer resistance to a disease or parasitic condition, for example, if a recombinant product is an anti-sense RNA molecule that specifically binds to an mRNA molecule encoding a polypeptide responsible for inflammation. Other examples of conferring resistance to diseases or parasites are described hereafter. In addition, examples of diseases are described hereafter.

Examples of parasites and strategies for conferring resistance to these parasites are described hereafter. These examples include, but are not limited to, worms, nematodes, insects, invertebrate, bacterial, viral, and eukaryotic parasites. These parasites can lead to diseased states that can be controlled by materials and methods of the invention.

The term "regulatory element" as used herein can refer to a DNA sequence that can increase or decrease an amount of product produced from another DNA sequence. A regulatory element can cause the constitutive production of the product (e.g., the product can be expressed constantly).

Alternatively, a regulatory element can enhance or diminish production of a recombinant product in an inducible fashion (e.g., the product can be expressed in response to a specific signal). A regulatory element can be controlled, for example, by nutrition, by light, or by adding a substance to the transgenic organism's system. Examples of regulatory elements well-known to those of ordinary skill in the art are promoters, enhancers, insulators, and repressors. See, e.g., *Transgenic Animals, Generation and Use*, 1997, Edited by L. M. Houdebine, Hardwood Academic Publishers, Australia, hereby incorporated herein by reference in its entirety including all figures, tables, and drawings.

The term "promoters" or "promoter" as used herein can refer to a DNA sequence that is located adjacent to a DNA sequence that encodes a recombinant product. A promoter is preferably linked operatively to an adjacent DNA sequence. A promoter typically increases an amount of recombinant product expressed from a DNA sequence as compared to an amount of the expressed recombinant product when no promoter exists. A promoter from one organism specie can be utilized to enhance recombinant product expression from a DNA sequence that originates from another organism specie. In addition, one promoter element can increase an amount of recombinant products expressed for multiple DNA sequences attached in tandem. Hence, one promoter element can enhance the expression of one or more recombinant products. Multiple promoter elements are well-known to persons of ordinary skill in the art. Examples of promoter elements are described hereafter.

The term "enhancers" or "enhancer" as used herein can refer to a DNA sequence that is located adjacent to the DNA sequence that encodes a recombinant product. Enhancer elements are typically located upstream of a promoter element or can be located downstream of a coding DNA sequence (e.g., a DNA sequence transcribed or translated into a recombinant product or products). Hence, an enhancer element can be located 100 base pairs, 200 base pairs, or 300 or more base pairs upstream of a DNA sequence that encodes recombinant product. Enhancer elements can increase an amount of recombinant product expressed from a DNA sequence above increased expression afforded by a promoter element. Multiple enhancer elements are readily available to persons of ordinary skill in the art.

The term "insulators" or "insulator" as used herein can refer to DNA sequences that flank the DNA sequence encoding the recombinant product. Insulator elements can direct recombinant product expression to specific tissues in an organism. Multiple insulator elements are well known to persons of ordinary skill in the art. See, e.g., Geyer, 1997, *Curr. Opin. Genet. Dev.* 7: 242–248, hereby incorporated herein by reference in its entirety, including all figures, tables, and drawings.

The term "repressor" or "repressor element" as used herein can refer to a DNA sequence located in proximity to the DNA sequence that encodes recombinant product, where a repressor sequence can decrease an amount of recombinant product expressed from that DNA sequence. Repressor elements can be controlled by binding of a specific molecule or specific molecules to a repressor element DNA sequence. These molecules can either activate or deactivate a repressor element. Multiple repressor elements are available to a person of ordinary skill in the art.

The terms "milk protein promoter," "urine protein promoter," "blood protein promoter," "lacrimal duct protein promoter," "synovial protein promoter," and "mandibular gland protein promoter" refer to promoter elements that regulate the specific expression of proteins within the specified fluid or gland or cell type in an animal. For example, a milk protein promoter is a regulatory element that can control expression of a protein that is expressed in milk of an animal. Other promoters, such as casein promoter, α-lactalbumin promoter, whey acid protein promoter, uroplakin promoter, and α-actin promoter, for example, are well known to a person of ordinary skill in the art.

In preferred embodiments, (1) the totipotent porcine cell is subject to manipulation; (2) the manipulation comprises the step of utilizing a totipotent porcine cell in a nuclear transfer procedure; (3) the manipulation comprises the step of cryopreserving totipotent cells; (4) the manipulation comprises the step of thawing totipotent cells; (5) the manipulation comprises the step of passaging totipotent cells; (6) the manipulation comprises the step of synchronizing totipotent cells; (7) the manipulation comprises the step of transfecting totipotent cells with foreign DNA; and (8) the manipulation comprises the step of dissociating a cell from another cell or group of cells.

The term "manipulation" as used herein can refer to common usage of the term, which is management or handling directed towards some object. Examples of manipulations are described herein.

The term "nuclear transfer" as used herein can refer to introducing a full complement of nuclear DNA from one cell to an enucleated cell. Nuclear transfer methods are well known to a person of ordinary skill in the art. See., e.g., Nagashima et al., 1997, *Mol. Reprod. Dev.* 48: 339–343; Nagashima et al., 1992, J. Reprod. Dev. 38: 73–78; Prather et al., 1989, *Biol. Reprod.* 41: 414–419; Prather et al., 1990, *Exp. Zool.* 255: 355–358; Saito et al., 1992, *Assis. Reprod. Tech. Andro.* 259: 257–266; and Terlouw et al., 1992, *Theriogenology* 37: 309, each of which is incorporated herein by reference in its entirety including all figures, tables and drawings. Nuclear transfer may be accomplished by using oocytes that are not surrounded by a zona pellucida.

The term "cryopreserving" as used herein can refer to freezing a cell, embryo, or animal of the invention. Cells, embryos, or portions of animals of the invention are frozen at temperatures preferably lower than 0° C., more preferably lower than −80° C., and most preferably at temperatures lower than −196° C. Cells and embryos of the invention can be cryopreserved for an indefinite amount of time. It is known that biological materials can be cryopreserved for more than fifty years and still remain viable. For example, bovine semen that is cryopreserved for more than fifty years can be utilized to artificially inseminate a female bovine animal and result in the birth of a live offspring. Methods and tools for cryopreservation are well-known to those skilled in the art. See, e.g., U.S. Pat. No. 5,160,312, entitled "Cryopreservation Process for Direct Transfer of Embryos," issued to Voelkel on Nov. 3, 1992.

The term "thawing" as used herein can refer to a process of increasing the temperature of a cryopreserved cell, embryo, or portions of animals. Methods of thawing cryopreserved materials such that they are active after a thawing process are well-known to those of ordinary skill in the art.

The terms "transfected" and "transfection" as used herein refer to methods of delivering exogenous DNA into a cell. These methods involve a variety of techniques, such as treating cells with high concentrations of salt, an electric field, liposomes, polycationic micelles, or detergent, to render a host cell outer membrane or wall permeable to nucleic acid molecules of interest. These specified methods are not limiting and the invention relates to any transformation technique well known to a person of ordinary skill in the art. See, e.g., *Molecular Cloning, a Laboratory Manual*, 2nd Ed., 1989, Sambrook, Fritsch, and Maniatis, Cold Spring Harbor Laboratory Press and *Transgenic Animals, Generation and Use*, 1997, Edited by L. M. Houdebine, Hardwood Academic Publishers, Australia, both of which were previously incorporated by reference.

The term "foreign DNA" as used herein can refer to DNA that can be transfected into a target cell, where foreign DNA harbors at least one base pair modification as compared to the nuclear DNA of the target organism. Foreign DNA and transfection can be further understood and defined in conjunction with the term "modified nuclear DNA," described previously.

The term "dissociating" as used herein can refer to materials and methods useful for separating a cell away from another cell, where the cells originally contacted one another. For example, a blastomere (i. e., a cellular member of a morula stage embryo) can be pulled away from the rest of a developing cell mass by techniques and apparatus well known to a person of ordinary skill in the art. See, e.g, U.S. Pat. No. 4,994,384, entitled "Multiplying Bovine Embryos," issued on Feb. 19, 1991, hereby incorporated herein by reference in its entirety, including all figures, tables, and drawings. Alternatively, cells proliferating in culture can be separated from one another to facilitate such processes as cell passaging and formation of EG cells, which are described herein. In addition, dissociation of a cultured cell from a group of cultured cells can be useful as a first step in a process of nuclear transfer, as described hereafter. When a cell is dissociated from an embryo, a dissociation can be useful for such processes as re-cloning, a process described herein, as well as a step for multiplying a number of embryos.

In another aspect, the invention features a totipotent porcine cell, prepared by a process comprising the steps of: (a) isolating at least one precursor cell; and (b) culturing the precursor cell in a cell culture media; where at least one cell in the culture media develops a morphology of an embryonic germ cell. In preferred embodiments, (1) the process comprises the step of introducing a stimulus to the precursor cell that converts the precursor cell into the totipotent porcine cell; (2) the process comprises the step of culturing the precursor cell in a cell culture medium that comprises a significant concentration of at least one carbohydrate; (3) the carbohydrate is glucose; and (4) the cell culture medium comprises one or more antibiotics.

The term "converts" as used herein can refer to the phenomenon in which precursor cells become totipotent. The term "convert" is synonymous with the term "reprogram" as used herein when the precursor cell is non-totipotent. Precursor cells can be converted into totipotent cells in varying proportions. For example, it is possible that only a small portion of precursor cells are converted into totipotent cells.

The term "stimulus" as used herein can refer to materials and/or methods useful for converting precursor cells into totipotent cells. A stimulus can be electrical, mechanical, temperature-related, and/or chemical, for example. The stimulus may be a combination of one or more different types of stimuli. A stimulus can be introduced to precursor cells for any period of time that accomplishes the conversion of precursor cells into totipotent cells.

The term "introduce" as used herein in reference to a stimulus can refer to a step or steps in which precursor cells are contacted with a stimulus. If a stimulus is chemical in nature, for example, such a stimulus may be introduced to precursor cells by mixing the stimulus with a cell culture medium.

The term "significant concentration of at least one carbohydrate" as used herein can refer to a cell culture medium having at least one carbohydrate in a concentration that does not lyse or shrink cultured cells. Cultured cells can lyse or shrink when osmotic pressure of a culture media is too great. Cells may tolerate a wide range of osmolarities (e.g., between 260 mOsm/kg and 320 mOsm/kg). Increasing concentrations of carbohydrates in culture media can dramatically increase osmotic pressure of a culture medium, which can effect cell viability. See, e.g., *Cells: a laboratory manual* (vol. 1), 1998, D. L. Spector, R. D. Goldman, L. A. Leinwand (eds.), Cold Spring Harbor Laboratory Press, hereby incorporated herein by reference in its entirety, including all figures, tables, and drawings.

A carbohydrate can be any monosaccharide, disaccharide, or polysaccharide known in the art. Examples of carbohydrates include, but are not limited to, glucose, mannose, dextrose, mannose, idose, galactose, talose, gulose, altrose, allose, ribose, arabinose, xylose, lyxose, threose, erythrose, glyceraldehyde, sucrose, lactose, maltose, cellulose, and glycogen. An especially preferred carbohydrate is glucose. Preferred concentrations of glucose in cell culture media are greater than 1 mM glucose, more greater than 5 mM glucose, 10 mM glucose, and 15 mM glucose, and most preferably about 17 mM glucose. The term "about" as used in relation to glucose concentrations can refer to plus or minus 2 mM glucose.

The term "antibiotic" as used herein can refer to any molecule that decreases growth rates of a bacterium, yeast, fungi, mold, or other contaminants in a cell culture. Antibiotics are optional components of cell culture media. Examples of antibiotics are well known in the art. See, Sigma and DIFCO catalogs.

In preferred embodiments (1) the precursor cells are co-cultured with feeder cells; (2) the precursor cells are not co-cultured with feeder cells; (3) the feeder cells are established from fetal cells; (4) the fetal cells arise from a fetus where no cell types have been removed from the fetus (e.g., the entire fetus is dissociated and placed in a cell culture system); (5) the fetal cells arise from a fetus where one or more cell types have been removed from the fetus (e.g., the head region is removed and the remaining fetus is dissociated and placed in a cell culture system); (6) a stimulus is introduced to precursor cells by feeder cells; (7) the feeder cells are the only source of the stimulus; (8) the stimulus is introduced to the precursor cells in a mechanical fashion; (9) the only stimulus that is introduced to the precursor cells is introduced in a mechanical fashion; (10) the stimulus is introduced to the precursor cells by feeder cells and in a mechanical fashion; (11) the stimulus comprises the step of incubating the precursor cells with a receptor ligand cocktail; (12) the precursor cells are isolated from an ungulate animal and preferably a porcine animal; (13) the precursor cells are selected from the group consisting of non-embryonic cells, non-fetal cells, differentiated cells, undifferentiated cells, somatic cells, embryonic cells, fetal cells, embryonic stem cells, primordial germ cells, genital ridge cells, cumulus cells, amniotic cells, fetal fibroblast cells, hepatacytes, embryonic germ cells, adult cells, cells isolated from an asynchronous population of cells, and cells isolated from a synchronized population of cells where the synchronous population is not arrested in the $G_0$ stage of the cell cycle; (14) the receptor ligand cocktail comprises at least one component selected from the group consisting of cytokine, growth factor, trophic factor, and neurotrophic factor, LIF, and FGF; (15) the LIF has an amino acid sequence substantially similar to the amino acid sequence of human LIF; and (16) the FGF has an amino acid sequence substantially similar to the amino acid sequence of bovine bFGF.

The terms "mechanical fashion" and "mechanical stimulus" as used herein can refer to introducing a stimulus to cells where the stimulus is not introduced by feeder cells. For example, purified LIF and bFGF (defined hereafter) can be introduced as a stimulus to precursor cells by adding these purified products to a cell culture medium in which the precursor cells are growing. Also as explained herein, a significant amount of glucose may be added to a culture medium as a stimulus to cells.

The term "feeder cells" as used herein can refer to cells that are maintained in culture and are co-cultured with target cells. Target cells can be precursor cells, embryonic stem cells, embryonic germ cells, cultured cells, and totipotent cells, for example. Feeder cells can provide, for example, peptides, polypeptides, electrical signals, organic molecules (e.g., steroids), nucleic acid molecules, growth factors (e.g., bFGF), other factors (e.g., cytokines such as LIF and steel factor), and metabolic nutrients to target cells. Certain cells, such as embryonic germ cells, cultured cells, and totipotent cells may not require feeder cells for healthy growth. Feeder cells preferably grow in a mono-layer.

Feeder cells can be established from multiple cell types. Examples of these cell types are fetal cells, mouse cells, Buffalo rat liver cells, and oviductal cells. These examples are not meant to be limiting. Tissue samples can be broken down to establish a feeder cell line by methods well known in the art (e.g., by using a blender). Feeder cells may originate from the same or different animal specie as precursor cells. Feeder cells can be established from ungulate fetal cells, porcine fetal cells, and murine fetal cells. One or more cell types can be removed from a fetus (e.g., primordial germs cells, cells in the head region, and cells in the body cavity region) and a feeder layer can be established from those cells that have been removed or cells in the remaining dismembered fetus. When an entire fetus is utilized to establish fetal feeder cells, feeder cells (e.g., fibroblast cells) and precursor cells (e.g., primordial germ cells) can arise from the same source (e.g., one fetus).

The term "receptor ligand cocktail" as used herein can refer to a mixture of one or more receptor ligands. A receptor ligand can refer to any molecule that binds to a receptor protein located on the outside or the inside of a cell. Receptor ligands can be selected from molecules of the cytokine family of ligands, neurotrophin family of ligands, growth factor family of ligands, and mitogen family of ligands, all of which are well known to a person of ordinary skill in the art. Examples of receptor/ligand pairs are: epidermal growth factor receptor/epidermal growth factor, insulin receptor/insulin, cAMP-dependent protein kinase/cAMP, growth hormone receptor/growth hormone, and steroid receptor/steroid. It has been shown that certain receptors exhibit cross-reactivity. For example, heterologous receptors, such as insulin-like growth factor receptor 1 (IGFR1) and insulin-like growth factor receptor 2 (IGFR2) can both bind IGF1. When a receptor ligand cocktail comprises a stimulus, the receptor ligand cocktail can be introduced to a precursor cell in a variety of manners known to a person of ordinary skill in the art.

The term "cytokine" as used herein can refer to a large family of receptor ligands well-known to a person of ordinary skill in the art. The cytokine family of receptor ligands includes such members as leukemia inhibitor factor (LIF); cardiotrophin 1 (CT-1); ciliary neurotrophic factor (CNTF); stem cell factor (SCF), which is also known as Steel factor; oncostatin M (OSM); and any member of the interleukin (IL) family, including IL-6, IL-1, and IL-12. The teachings of the invention do not require the mechanical addition of steel factor (also known as stem cell factor in the art) for the conversion of precursor cells into totipotent cells.

The term "growth factor" as used herein can refer to any receptor ligand that may cause a cell growth effect, may cause a cell proliferation effect, and/or may effect cell morphology. Examples of growth factors are well known in the art. Fibroblast growth factor (FGF) is one example of a growth factor. The term "bFGF" can refer to basic FGF.

The term "substantially similar" as used herein in reference to amino acid sequences can refer to two amino acid sequences having preferably 50% or more amino acid identity, more preferably 70% or more amino acid identity or most preferably 90% or more amino acid identity. Amino acid identity is a property of amino acid sequence that measures their similarity or relationship. Identity is measured by dividing the number of identical residues in the two sequences by the total number of residues and multiplying the product by 100. Thus, two copies of exactly the same sequence have 100% identity, while sequences that are less highly conserved and have deletions, additions, or replacements have a lower degree of identity. Those of ordinary skill in the art will recognize that several computer programs are available for performing sequence comparisons and determining sequence identity.

When precursor cells are cultured in vitro, it has been discovered that precursor cells can give rise to cells having a different cell morphology than the precursor cells without introducing the precursor cells to a stimulus. For example, it has been discovered that precursor genital ridge cells can develop into cells having EG cell morphology without contacting the precursor cells with feeder cells, a receptor ligand, or a growth factor. Thus, in preferred embodiments, (1) precursor cells are not contacted with exogenous receptor ligand; (2) precursor cells are not contacted with exogenous growth factor; (3) precursor cells are not contacted with feeder cells; (4) precursor cells are not contacted with exogenous receptor ligand and are not contacted with exogenous growth factor; (5) precursor cells are not contacted with exogenous receptor ligand and are not contacted with feeder cells; (6) precursor cells are not contacted with exogenous growth factor and are not contacted with feeder cells; and (7) precursor cells are not contacted with exogenous receptor ligand and are not contacted with exogenous growth factor and are not contacted with feeder cells.

The term "exogenous" as used herein in reference to growth factor or receptor ligand can refer to an outside source of a receptor ligand and/or growth factor that may be added to a substrate or medium that is in contact with target cells. For example, purified bFGF that is commercially available to a person of ordinary skill in the art may be added to cell culture media that contacts precursor cells. In this latter example, such purified bFGF can be referred to as "exogenous bFGF." Multiple exogenous receptor ligands and/or multiple exogenous growth factors or combinations thereof may be added to a liquid medium contacting cells. Alternatively, it may not be required that precursor cells are contacted with exogenous growth factor or exogenous receptor ligand, as discussed previously.

In another aspect, the invention features a method for preparing a totipotent porcine cell, comprising the following steps: (a) isolating one or more precursor cells; and (b) introducing the precursor cell to a stimulus that converts the precursor cell into the totipotent cell. Any of the embodiments defined previously herein in reference to totipotent porcine cells relate to methods for preparing totipotent porcine cells. In yet another aspect, the invention features a method for preparing a totipotent porcine cell, comprising the following steps: (a) isolating at least one precursor cell; and (b) culturing the precursor cell in a cell culture media to establish the totipotent cell; where the totipotent cell has a morphology of an embryonic germ cell.

Cloned Embrvos of the Invention

The invention relates in part to a cloned totipotent porcine embryo. Hence, aspects of the invention feature a cloned porcine embryo where (1) the embryo is totipotent; (2) the embryo arises from a totipotent cell; (3) the embryo arises from a non-embryonic porcine cell; and (4) any combination of the foregoing.

The term "totipotent" as used herein in reference to embryos can refer to embryos that can develop into a live born porcine animal. The term "live born" is defined previously.

The term "cloned" as used herein can refer to a cell, embryonic cell, fetal cell, and/or animal cell having a nuclear DNA sequence that is substantially similar or identical to a nuclear DNA sequence of another cell, embryonic cell, fetal cell, and/or animal cell. The terms "substantially similar" and "identical" are described herein. A cloned embryo can arise from one nuclear transfer process, or alternatively, a cloned embryo can arise from a cloning process that includes at least one re-cloning step. If a cloned embryo arises from a cloning procedure that includes at least one re-cloning step, then the cloned embryo can indirectly arise from a totipotent cell since the re-cloning step can utilize embryonic cells isolated from an embryo that arose from a totipotent cell.

In preferred embodiments (1) the cloned porcine embryo can be one member of a plurality of embryos, where the plurality of embryos share a substantially similar nuclear DNA sequence; (2) the cloned porcine embryo can be one member of a plurality of embryos, and the plurality of embryos can have an identical nuclear DNA sequence; (3) the cloned porcine embryo has a nuclear DNA sequence that is substantially similar to a nuclear DNA sequence of a live born porcine animal; (4) one or more cells of the cloned porcine embryo have modified nuclear DNA; (5) the cloned porcine embryo is subject to manipulation; (6) the manipulation comprises the step of culturing the embryo in a suitable medium; (7) the medium can comprise feeder cells; (8) the manipulation of an embryo comprises the step of implanting the embryo into reproductive tract of a female animal; (9) the female animal is preferably an ungulate animal and more preferably a porcine animal; (10) the estrus cycle of the female is synchronized with the development cycle of the embryo; and (11) the manipulation comprises the step of incubating the embryo in an artificial environment.

All preferred embodiments related to modified nuclear DNA for totipotent cells of the invention extend to cloned embryos of the invention. In addition, any of the manipulations described in conjunction with totipotent cells of the invention apply to cloned embryos of the invention.

The term "substantially similar" as used herein in reference to nuclear DNA sequences refer to two nuclear DNA sequences that are nearly identical. Two sequences may differ by copy error differences that normally occur during replication of nuclear DNA. Substantially similar DNA sequences are preferably greater than 97% identical, more preferably greater than 98% identical, and most preferably greater than 99% identical. The term "identity" as used herein in reference to nuclear DNA sequences can refer to usage of the term in reference to amino acid sequences, which is described previously herein. It is preferred and expected that nuclear DNA sequences are identical for cloned animals. Examples of methods for determining whether cloned animals and cells from which they are cloned have substantially similar or identical nuclear DNA sequences are microsattelite analysis and DNA fingerprinting analysis. Ashworth et al., 1998, *Nature* 394: 329 and Signer et al., 1998, *Nature* 394: 329.

The term "plurality" as used herein in reference to embryos can refer to a set of embryos having a substantially similar nuclear DNA sequence. In preferred embodiments, a plurality consists of five or more embryos, ten or more embryos, fifteen or more embryos, twenty or more embryos, fifty or more embryos, seventyfive or more embryos, one-hundred or more embryos, and one-thousand or more embryos.

The term "culturing" as used herein with respect to embryos can refer to laboratory procedures that involve placing an embryo in a culture medium. An embryo can be placed in a culture medium for an appropriate amount of time to allow stasis of an embryo, or to allow the embryo to grow in the medium. Culture media suitable for culturing embryos are well-known to those skilled in the art. See, e.g., Nagashima et al., 1997, *Mol. Reprod. Dev.* 48: 339–343; Petters & Wells, 1993, *J. Reprod. Fert.* (*Suppl*) 48: 61–73; Reed et al., 1992, *Theriogenology* 37: 95–109; Dobrinsky et al., 1996, *Biol. Reprod.* 55: 1069–1074; U.S. Pat. No. 5,213,979, First et al., "In Vitro Culture of Bovine Embryos," May 25, 1993; U.S. Pat. No. 5,096,822, Rosenkrans, Jr. et al., "Bovine Embryo Medium," Mar. 17, 1992, each of which is incorporated herein by reference in its entirety, including all figures, tables, and drawings.

The term "suitable medium" as used herein can refer to any medium that allows cell proliferation or allows stasis of an embryo. If a medium allows cell proliferation, a suitable medium need not promote maximum proliferation, only measurable cell proliferation. A suitable medium for embryo development can be an embryo culture medium described herein by example. The term "feeder cells" is defined previously herein. Embryos of the invention can be cultured in media with or without feeder cells. In other preferred embodiments, the feeder cells can be cumulus cells.

The term "implanting" as used herein in reference to embryos can refer to impregnating a female animal with an embryo described herein. Implanting techniques are well known to a person of ordinary skill in the art. See, e.g., Polge & Day, 1982, "Embryo transplantation and preservation," *Control of Pig Reproduction*, DJA Cole and GR Foxcroft, eds., London, UK, Butterworths, pp. 227–291; Gordon, 1997, "Embryo transfer and associated techniques in pigs," *Controlled reproduction in pigs* (Gordon, ed), CAB International, Wallingford UK, pp 164–182; and Kojima, 1998, "Embryo transfer," *Manual of pig embryo transfer Procedures*, National Livestock Breeding Center, Japanese Society for Development of Swine Technology, pp 76–79, each of which is incorporated herein by reference in its entirety, including all figures, tables, and drawings.

The embryo may be allowed to develop in utero, or alternatively, the fetus may be removed from the uterine environment before parturition.

The term "synchronized" as used herein in reference to estrus cycle, can refer to assisted reproductive techniques well known to a person of ordinary skill in the art. These techniques are fully described in the reference cited in the previous paragraph. Typically, estrogen and progesterone hormones are utilized to synchronize the estrus cycle of the female animal with the developmental stage of the embryo. The term "developmental stage" as used herein can refer to embryos of the invention and morphological and biochemical changes during embryo development. This developmental process is predictable for embryos from ungulates, and can be synchronized with the estrus cycle of a recipient animal. A procedure for synchronizing a female porcine animal is set forth hereafter.

The term "artificial environment" refers to one that promotes development of an embryo or other developing cell mass. An artificial environment can be a uterine environment or an oviductal environment of a species different from that of a developing cell mass. For example, a developing bovine embryo can be placed into an uterus or oviduct of an ovine animal. Stice & Keefer, 1993, "Multiple generational bovine embryo cloning," *Biology of Reproduction* 48: 715–719. Alternatively, an artificial development environment can be assembled in vitro. This type of artificial uterine environment can be synthesized using biological and chemical components known in the art.

In another aspect the invention features a cloned mammalian embryo, where the embryo is totipotent, prepared by a process comprising the step of nuclear transfer. Preferably, nuclear transfer occurs between (a) a nuclear donor, and (b) an oocyte, where the oocyte is at a stage allowing formation of the embryo.

In preferred embodiments, (1) the oocyte is an enucleated oocyte; (2) the oocyte preferably originates from an ungulate animal and more preferably originate from a porcine animal; (3) the oocyte has been matured; (4) the oocyte has been matured for more than 48 hours; (5) the oocyte has been matured for about 53 hours; (6) the nuclear donor is placed in the perivitelline space of the oocyte; (7) the nuclear donor utilized for nuclear transfer can arise from any of the cells described previously (e.g., a non-embryonic cell, a primordial germ cell, a genital ridge cell, a differentiated cell, a fetal cell, a non-fetal cell, a non-primordial germ cell, a cell isolated from an asynchronous population of cells, a cell isolated from a synchronous population of cells, a cell isolated from an existing animal, an embryonic stem cell, an embryonic germ cell, an amniotic cell, a cumulus cell, and a fetal fibroblast cell); (8) the nuclear transfer comprises the step of translocation of the nuclear donor into the recipient oocyte; (9) the translocation can comprise the step of injection of the nuclear donor into the recipient oocyte; (10) the translocation can comprise the step of fusion of the nuclear donor and the oocyte; (11) the fusion can comprise the step of delivering one or more electrical pulses to the nuclear donor and the oocyte; (12) the fusion can comprise the step of delivering a suitable concentration of at least one fusion agent to the nuclear donor and the oocyte; (13) the nuclear transfer may comprise the step of activation of the nuclear donor and the oocyte; (14) the activation is accomplished by (i) increasing intracellular levels of divalent cations in a cell, and (ii) reducing phosphorylation of cellular proteins in the cell; (15) the activation is accomplished by (i) introducing a divalent ion ionophore to a cell, and (ii) introducing a protein kinase inhibitor to a cell; (16) the divalent ion ionophore is a $Ca^{2+}$ ionophore; (17) the $Ca^{2+}$ ionophore is ionomycin; (18) the protein kinase inhibitor is DMAP; and (19) activation is accomplished by introducing DMAP and ionomycin to a cell.

The term "nuclear donor" as used herein can refer to a cell or a nucleus from a cell that is translocated into a nuclear acceptor. A nuclear donor may be a totipotent porcine cell. In addition, a nuclear donor may be any cell described herein, including, but not limited to a non-embryonic cell, a non-fetal cell, a differentiated cell, a somatic cell, an embryonic cell, a fetal cell, an embryonic stem cell, a primordial germ cell, a genital ridge cell, a cumulus cell, an amniotic cell, a fetal fibroblast cell, a hepatacyte, an embryonic germ cell, an adult cell, a cell isolated from an asynchronous population of cells, and a cell isolated from a synchronized population of cells where the synchronous population is not arrested in the $G_0$ stage of the cell cycle. A nuclear donor cell can also be a cell that has differentiated from an embryonic stem cell. See, e.g., Piedrahita et al., 1998, *Biol. Reprod* 58: 1321–1329; Shim et al., 1997, *Biol. Reprod.* 57: 1089–1095; Tsung et al., 1995, *Shih Yen Sheng Wu Hsueh Pao* 28: 173–189; and Wheeler, 1994, *Reprod Fertil. Dev.* 6: 563–568, each of which is incorporated herein by reference in its entirety including all figures, drawings, and tables. In addition, a nuclear donor may be a cell that was previously frozen or cryopreserved.

The term "enucleated oocyte" as used herein can refer to an oocyte which has had its nucleus removed. Typically, a needle can be placed into an oocyte and the nucleus can be aspirated into the needle. The needle can be removed from the oocyte without rupturing the plasma membrane. This enucleation technique is well known to a person of ordinary skill in the art. See, U.S. Pat. No. 4,994,384; U.S. Pat. No. 5,057,420; and Willadsen, 1986, *Nature* 320:63–65. An enucleated oocyte is preferably prepared from an oocyte that has been matured for greater than 24 hours, preferably matured for greater than 36 yours, more preferably matured for greater than 48 hours, and most preferably matured for about 53 hours.

The terms "maturation" and "matured" as used herein can refer to a process in which an oocyte is incubated in a medium in vitro. Maturation media can contain multiple types of components, including hormones and growth factors. Time of maturation can be determined from the time that an oocyte is placed in a maturation medium to the time that the oocyte is subject to a manipulation (e.g., enucleation, nuclear transfer, fusion, and/or activation). Oocytes can be matured in multiple media well known to a person of ordinary skill in the art. See, e.g., Mattioli et al., 1989, *Theriogenology* 31: 1201–1207; Jolliff & Prather, 1997, *Biol. Reprod.* 56: 544–548; Funahashi & Day, 1993, *J. Reprod. Fert.* 98: 179–185; Nagashima et al., 1997, *Mol. Reprod. Dev.* 38: 339–343; Abeydeera et al., 1998, *Biol. Reprod.* 58: 213–218; Funahashi et al., 1997, *Biol. Reprod.* 57: 49–53; and Sawai et al., 1997, *Biol. Reprod.* 57: 1–6, each of which is incorporated herein by reference in its entirety, including all figures, tables, and drawings. Oocytes can be matured for any period of time: an oocyte can be matured for greater than 10 hours, greater than 20 hours, greater than 24 hours, greater than 60 hours, greater than 72 hours, greater than 90 hours, preferably matured for greater than 36 hours, more preferably matured for greater than 48 hours, and most preferably matured for about 53 hours. The term "about" with respect to oocyte maturation can refer to plus or minus 3 hours.

An oocyte can also be matured in vivo. Time of maturation may be the time that an oocyte receives an appropriate stimulus to resume meiosis to the time that the oocyte is manipulated. Similar maturation periods described above for in vitro matured oocytes apply to in vivo matured oocytes.

A variety of oocytes can be selected for maturation. For example, oocytes can be isolated from a pre-pubertal porcine animal or a peri-pubertal animal (e.g., a sow). However, oocytes from pre-pubertal porcine animals may be incapable of spontaneous resumption of meiosis in vitro. It is a preferred embodiment of the invention that oocytes isolated from a sow are utilized for maturation and eventually in nuclear transfer procedures.

Nuclear transfer may be accomplished by combining one nuclear donor and more than one enucleated oocyte. In addition, nuclear transfer may be accomplished by combining one nuclear donor, one or more enucleated oocytes, and the cytoplasm of one or more enucleated oocytes.

The term "cybrid" as used herein can refer to an oocyte having a nuclear donor inserted within. The term "cybrid" can refer to an oocyte having a nuclear donor that is translocated into the oocyte. A nuclear donor may be fused with an oocyte, and the term "cybrid" includes oocytes that are not fused with a nuclear donor.

The invention relates in part to cloned mammalian embryos established by nuclear transfer of a nuclear donor and an non-enucleated oocyte. A cloned embryo may be established where nuclear DNA from the donor cell replicates during cellular divisions while nuclear DNA from an oocyte does not replicate. See, e.g., Wagoner et al., 1996, "Functional enucleation of bovine oocytes: effects of centrifugation and ultraviolet light," *Theriogenology* 46: 279–284.

The term "another ungulate" as used herein can refer to a situation where a nuclear donor originates from an ungulate of a different species, genera or family than the ungulate from which the recipient oocyte originates. For example, a porcine cell can be used as a nuclear donor, while a recipient oocyte can be isolated from a domestic cow. This example is not meant to be limiting and any ungulate species/family combination of nuclear donors and recipient oocytes are foreseen by the invention.

The term "translocation" as used herein in reference to nuclear transfer can refer to combining a nuclear donor and a recipient oocyte. Translocation may be performed by such techniques as fusion and/or direct injection, for example.

The term "injection" as used herein in reference to embryos, can refer to perforation of an oocyte with a needle, and insertion of a nuclear donor in the needle into the oocyte. In preferred embodiments, a nuclear donor may be injected into the cytoplasm of an oocyte or in the perivitelline space of an oocyte. This direct injection approach is well known to a person of ordinary skill in the art, as indicated by publications already incorporated herein in reference to nuclear transfer. For a direct injection approach to nuclear transfer, a whole cell may be injected into an oocyte, or alternatively, a nucleus isolated from a cell may be injected into an oocyte. Such an isolated nucleus may be surrounded by nuclear membrane only, or the isolated nucleus may be surrounded by nuclear membrane and plasma membrane in any proportion. An oocyte may be pre-treated to enhance the strength of its plasma membrane, such as by incubating the oocyte in sucrose prior to injection of a nuclear donor.

Techniques for placing a nuclear donor into the perivitelline space of an enucleated oocyte is well known to a person of ordinary skill in the art, and is fully described in patents and references cited previously herein in reference to nuclear transfer.

The term "fusion" as used herein can refer to combination of portions of lipid membranes corresponding to a nuclear donor and a recipient oocyte. Lipid membranes can correspond to plasma membranes of cells or nuclear membranes, for example. Fusion can occur with addition of a fusion stimulus between a nuclear donor and recipient oocyte when they are placed adjacent to one another, or when a nuclear donor is placed in the perivitelline space of a recipient oocyte, for example. Specific examples for translocation of a porcine mammalian cell into an oocyte are described hereafter in other preferred embodiments. These techniques for translocation are fully described in references cited previously herein in reference to nuclear transfer.

The term "electrical pulses" as used herein can refer to subjecting a nuclear donor and recipient oocyte to electric current. For nuclear transfer, a nuclear donor and recipient oocyte can be aligned between electrodes and subjected to electrical current. Electrical current can be alternating current or direct current. Electrical current can be delivered to cells for a variety of different times as one pulse or as multiple pulses. Cells are typically cultured in a suitable medium for delivery of electrical pulses. Examples of electrical pulse conditions utilized for nuclear transfer are described in references and patents previously cited herein in reference to nuclear transfer.

The term "fusion agent" as used herein can refer to any compound or biological organism that can increase the probability that portions of plasma membranes from different cells will fuse when a nuclear donor is placed adjacent to a recipient oocyte. In preferred embodiments fusion agents are selected from the group consisting of polyethylene glycol (PEG), trypsin, dimethylsulfoxide (DMSO), lectins, agglutinin, viruses, and Sendai virus. These examples are not meant to be limiting and other fusion agents known in the art are applicable and included herein.

The term "suitable concentration" as used herein in reference to fusion agents, can refer to any concentration of a fusion agent that affords a measurable amount of fusion. Fusion can be measured by multiple techniques well known to a person of ordinary skill in the art, such as by utilizing a light microscope, dyes, and fluorescent lipids, for example.

The term "activation" can refer to any materials and methods useful for stimulating a cell to divide before, during, and after a nuclear transfer step. The term "cell" as used in the previous sentence can refer to an oocyte, a cybrid, a nuclear donor, and an early stage embryo. These types of cells may require stimulation in order to divide after nuclear transfer has occurred. The invention pertains to any activation materials and methods known to a person of ordinary skill in the art.

Although electrical pulses are sometimes sufficient for stimulating activation of cells, other non-electrical means for activation are useful and are often necessary for proper activation of a cell. Chemical materials and methods useful for nonelectrical activation are described below in other preferred embodiments of the invention. When two or more chemical components are introduced to a cell for activating the cell, the components can be added simultaneously or in steps.

Examples of electrical processes for activation are well known in the art. Researchers have also reported non-electrical processes for activation. See, e.g., Grocholová et al., 1997, *J. Exp. Zoology* 277: 49–56; Schoenbeck et al., 1993, *Theriogenology* 40: 257–266; Prather et al., 1989, *Biology of Reproduction* 41: 414–418; Prather et al., 1991, *Molecular Reproduction and Development* 28: 405–409; Mattioli et al., 1991, *Molecular Reproduction and Development* 30: 109–125; Terlouw et al., 1992, *Theriogenology* 37: 309; Prochazka et al., 1992, *J. Reprod. Fert.* 96: 725–734; Funahashi et al., 1993, *Molecular Reproduction and Development* 36: 361–367; Prather et al., *Bio. Rep. Vol.* 50 *Sup* 1: 282; Nussbaum et al., 1995, *Molecular Reproduction and Development* 41: 70–75; Funahashi et al., 1995, *Zygote* 3: 273–281; Wang et al., 1997, *Biology of Reproduction* 56: 1376–1382; Piedrahita et al., 1989, *Biology of Reproduction* 58: 1321–1329; Macháty et al., 1997, *Biology of Reproduction* 57: 85–91; and Macháty et al., 1995, *Biology of Reproduction* 52: 753–758.

Examples of components that are useful for non-electrical activation include ethanol; inositol trisphosphate (IP$_3$); divalent ions (e.g., addition of Ca$^{2+}$ and/or Sr$^{2+}$); microtubule inhibitors (e.g., cytochalasin B); ionophores for divalent ions (e.g., the Ca$^{3+}$ ionophore ionomycin); protein kinase inhibitors (e.g., 6-dimethylaminopurine (DMAP)); protein synthesis inhibitors (e.g., cyclohexamide); phorbol esters such as phorbol 12-myristate 13-acetate (PMA); and thapsigargin. It is also known that temperature change and mechanical techniques are also useful for non-electrical activation. The invention includes any activation techniques known in the art. See, e.g., U.S. Pat. No. 5,496,720, entitled "Parthenogenic Oocyte Activation," issued on Mar. 5, 1996, Susko-Parrish et al., and Wakayama et al., 1998, *Nature* 394: 369–374, each of which is incorporated herein by reference in its entirety, including all figures, tables, and drawings.

When ionomycin and DMAP are utilized for non-electrical activation, ionomycin and DMAP may be introduced to cells simultaneously or in a step-wise addition, the latter being a preferred mode as described herein. Preferred concentrations of ionomycin and DMAP are 0.5 μM ionomycin to 50 μM ionomycin and 0.5 mM DMAP to 50 mM DMAP, more preferably 1 μM ionomycin to 20 μM ionomycin and 1 mM DMAP to 5 mM DMAP, and most preferably about 10 μM ionomycin and about 2 mM DMAP, where the term "about" can refer to plus or minus 2 μM ionomycin and 1 mM DMAP.

In other preferred embodiments, (1) one or more cells of the cloned porcine embryo comprise modified nuclear DNA; (2) the cloned porcine embryo is subject to manipulation; (3) the manipulation comprises the step of disaggregating at least one individual cell from a cloned embryo; (4) the manipulation comprises the step of utilizing the individual cell as a nuclear donor in a nuclear transfer procedure; (5) the individual cell is disaggregated from the inner cell mass of a blastocyst stage embryo; (6) the individual cell is disaggregated from a pre-blastocyst stage embryo; (7) the manipulation comprises the process of re-cloning; (8) the re-cloning process comprises the steps of: (a) separating the embryo into one or more individual cells, and (b) performing at least one subsequent nuclear transfer between (i) an individual cell of (a), and (ii) an oocyte; (9) the individual cell is placed in the perivitelline space of the enucleated oocyte for the subsequent nuclear transfer; (10) the subsequent nuclear transfer comprises at least one of the steps of translocation, injection, fusion, and activation of the individual cell and/or the enucleated oocyte; (11) one or more cells of the cloned mammalian embryo arising from the subsequent nuclear transfer comprises modified nuclear DNA; and (12) the cloned mammalian embryo arising from the subsequent nuclear transfer may be subject to a subsequent manipulation, where the subsequent manipulation is any of the manipulation steps defined previously herein in relation to totipotent cells and/or cloned embryos.

The term "individual cells" as used herein can refer to cells that have been isolated from a cloned mammalian embryo of the invention. An individual single cell can be isolated from an embryo by techniques well known to those skilled in the art, as discussed in references cited previously herein.

The term "subsequent nuclear transfer" as described herein is also referred to as a "re-cloning" step. Preferably, a re-cloning step can be utilized to enhance nuclear reprogramming during nuclear transfer, such that a product of nuclear transfer is a live born animal. The number of subsequent nuclear transfer steps is discussed in greater detail hereafter.

Any of the preferred embodiments related to the translocation, injection, fusion, and activation steps described previously herein can relate to any subsequent nuclear transfer step.

The term "inner cell mass" as used herein can refer to cells that give rise to the embryo proper. Cells that line the outside of a blastocyst can be referred to as a trophoblast of the embryo. Methods for isolating inner cell mass cells from an embryo are well known to a person of ordinary skill in the art, as discussed previously. The term "pre-blastocyst" is well known in the art and is referred to previously.

The term "ovulated in vivo" as used herein can refer to an oocyte that is isolated from an animal a certain number of hours after the animal exhibits characteristics that is associated with estrus or following injection of exogenous gonadatrophins known to induce ovulation. The characteristics of an animal in estrus are well known to a person of ordinary skill in the art, as described in references disclosed herein. See, e.g., Gordon, 1977, "Embryo transfer and associated techniques in pigs (Gordon, ed.)," *CAB International, Wallingford UK*, pp. 60–76 and Kojima, 1998, "Embryo transfer," *Manual of pig embryo transfer procedures*, National Livestock Breeding Center, Japanese Society for Development of Swine Technology, pp. 7–21, each of which is incorporated herein by reference in its entirety including all figures, tables, and drawings.

In another aspect the invention relates to a cloned porcine embryo produced by a process comprising the steps of (a) translocation of a nuclear donor into an oocyte to establish a nuclear transfer oocyte; and (b) non-electrical activation of the nuclear transfer oocyte to establish the porcine embryo.

In preferred embodiments, (1) the nuclear donor is a cultured cell and is selected from any of the cell types described herein; (2) the nuclear donor is a totipotent cell or is isolated from a totipotent cell; (3) the nuclear donor is any cell type discussed herein (e.g., embryonic germ cell, cumulus cell, amniotic cell, fibroblast cell); (4) the translocation comprises the step of fusion; and (5) the process comprises the step of culturing the embryo in vitro. Any other preferred embodiments discussed herein with respect to porcine embryos, and especially with regard to activation, pertains to this aspect of the invention.

In another aspect the invention relates to a method for preparing a cloned porcine embryo. The method comprises the step of a nuclear transfer between: (a) a nuclear donor, where the nuclear donor is a totipotent porcine cell; and (b) an oocyte, where the oocyte is at a stage allowing formation of the embryo. In yet another aspect the invention relates to a method for cloning a porcine embryo, comprising the steps of (a) translocation of a nuclear donor into an oocyte to establish a nuclear transfer oocyte; and (b) non-electrical activation of the nuclear transfer oocyte to establish the porcine embryo. In preferred embodiments, any of the embodiments of the invention concerning cloned porcine embryos apply to methods for preparing cloned porcine embryos.

Cloned Fetuses of the Invention

In another aspect, the invention features a cloned porcine fetus arising from a totipotent embryo of the invention. A fetus may be isolated from an uterus of a pregnant female animal and may be isolated from another part of a pregnant female animal in the case of an ectopic pregnancy.

In preferred embodiments, (1) one or more cells of the fetus harbor modified nuclear DNA (defined previously herein); and (2) the fetus may be subjected to any of the manipulations defined herein. For example, one manipulation may comprise the steps of isolating a fetus from the uterus of a pregnant female animal, isolating a cell from the fetus (e.g., a primordial germ cell), and utilizing the isolated cell as a nuclear donor for nuclear transfer.

Other aspects of the invention feature (1) a cloned porcine fetus prepared by a process comprising the steps of (a) preparation of a cloned porcine embryo defined previously, and (b) manipulation of the cloned porcine embryo such that it develops into a fetus; (2) a method for preparing a cloned porcine fetus comprising the steps of (a) preparation of a cloned porcine embryo defined previously, and (b) manipulation of the cloned porcine embryo such that it develops into a fetus; (3) a method of using a cloned fetus of the invention comprising the step of isolating at least one cell type from a fetus (e.g., for establishing a feeder cell layer); and (4) a method of using a cloned fetus of the invention comprising the step of separating at least one part of a fetus into individual cells (e.g., for establishing a feeder cell layer).

Cloned Porcine Animals of the Invention

In another aspect the invention features a cloned porcine animal arising from a totipotent porcine cell of the invention. A cloned porcine animal can develop from a cloned embryo that is established by a nuclear transfer process between a totipotent porcine cell and an oocyte. A totipotent porcine cell is preferably established by utilizing any of the materials and methods described previously herein.

In yet another aspect the invention relates to a cloned porcine animal, where the animal is one member of a plurality of porcine animals, and where the plurality of animals have a substantially similar nuclear DNA sequence. The term "substantially similar" in relation to nuclear DNA sequences is defined previously herein.

In preferred embodiments, (1) the plurality consists of five or more animals, ten or more animals, one-hundred or more animals, and one-thousand or more animals; and (2) the plurality of animals can have an identical nuclear DNA sequence. The term "identical" in reference to nuclear DNA sequences is described previously herein.

In another aspect, the invention relates to a cloned porcine animal having one or more cells that comprise modified nuclear DNA. All of the preferred embodiments relating to modified nuclear DNA described previously apply to cloned porcine animals of the invention.

In yet another aspect, the invention features a method of using a cloned porcine animal, comprising the step of isolating at least one component from the porcine animal.

The term "component" as used herein can relate to any portion of a porcine animal. A component can be selected from the group consisting of fluid, biological fluid, cell, tissue, organ, gamete, embryo, and fetus. For example, precursor cells, as defined previously, may arise from fluids, biological fluids, cells, tissues, organs, gametes, embryos, and fetuses isolated from cloned organisms of the invention.

The term "gamete" as used herein can refer to any cell participating, directly or indirectly, to the reproductive system of an animal. A gamete can be a specialized product from the gonads of an organism, where the gamete may transfer genetic material while participating in fertilization. Examples of gametes are spermatocytes, spermatogonia, oocytes, and oogonia. Gametes can be present in fluids, tissues, and organs collected from animals (e.g., sperm is present in semen). The invention relates to collection of any type of gamete from an animal. For example, methods of collecting semen and oocytes are known to a person of ordinary skill in the art. See, e.g., Gordon, 1997, "Introduction to controlled breeding in pigs, Embryo transfer and associated techniques in pigs," *Controlled reproduction in pigs* (Gordon, ed.), CAB International, Wallingford UK, pp. 1–59; Mattioli et al., 1989, *Theriogenology* 31: 1207–1207; Funahashi & Day, 1993, *J. Reprod. Fert.* 98 179–185; Funahashi et al., 1997, *Biol Reprod.* 57: 49–53; Abeydeera et al., 1998, *Biol. Reprod.* 58: 213–218; and Sawai et al., 1997, *Biol. Reprod.* 57: 1–6, each of which is incorporated herein by reference in its entirety including all figures, tables, and drawings.

The term "tissue" is defined previously. The term "organ" relates to any organ isolated from an animal or any portion of an organ. Examples of organs and tissues are neuronal tissue, brain tissue, spleen, heart, lung, gallbladder, pancreas, testis, ovary and kidney. These examples are not limiting and the invention relates to any organ and any tissue isolated from a cloned animal of the invention.

In a preferred embodiments, the invention relates to (1) fluids, biological fluids, cells, tissues, organs, gametes, embryos, and fetuses can be subject to manipulation; (2) the manipulation can comprise the step of cryopreserving the gametes, embryos, and/or fetal tissues; (3) the manipulation can comprise the step of thawing the cryopreserved items; (4) the manipulation can comprise the step of separating the semen into X-chromosome bearing semen and Y-chromosome bearing semen; (5) the manipulation comprises methods of preparing the semen for artificial insemination; (6) the manipulation comprises the step of purification of a desired polypeptide(s) from the biological fluid or tissue; (7) the manipulation comprises concentration of the biological fluids or tissues; (8) the manipulation can comprise the step of transferring one or more fluids, cloned cells, cloned tissues, cloned organs, and/or portions of cloned organs to a recipient organism (e.g., the recipient organism may be of a different specie than the donor source); (9) the recipient organism is non-human; and (10) the recipient organism is human.

The term "separating" as used herein in reference to separating semen can refer to methods well known to a person skilled in the art for fractionating a semen sample into sex-specific fractions. This type of separation can be accomplished by using flow cytometers that are commercially available. Methods of utilizing flow cytometers from separating sperm by genetic content are well known in the art. In addition, semen can be separated by its sex-associated characteristics by other methods well known to a person of ordinary skill in the art. See, U.S. Pat. Nos. 5,439,362, 5,346,990, and 5,021,244, entitled "Sex-Associated Membrane Proteins and Methods for Increasing the Probability that Offspring Will Be of a Desired Sex," Spaulding, issued on Aug. 8, 1995, Sep. 13, 1994, and Jun. 4, 1991respectively, each of which is incorporated herein by reference in its entirety including all figures, tables, and drawings.

The term "purification" as used herein can refer to increasing the specific activity of a particular polypeptide or polypeptides in a sample. Specific activity can be expressed as a ratio between the activity or amount of a target polypeptide and the concentration of total polypeptide in the sample. Activity can be catalytic activity and/or binding activity, for example. Also, specific activity can be expressed as a ratio between the concentration of target polypeptide and the concentration of total polypeptide. Purification methods include dialysis, centrifugation, and column chromatography techniques, which are well-known procedures to a person of ordinary skill in the art. See, e.g., Young et al., 1997, "Production of biopharmaceutical proteins in the milk of transgenic dairy animals," *BioPharm* 10(6): 34–38.

The term "transferring" as used herein can relate to shifting a group of cells, tissues, organs, and/or portions of organs to an animal. Cells, tissues, organs, and/or portions of organs can be, for example, (a) developed in vitro and then transferred to an animal, (b) removed from a cloned porcine animal and transferred to another animal of a different specie, (c) removed from a cloned porcine animal and transferred to another animal of the same specie, (d) removed from one portion of an animal (e.g., cells from a leg of an animal) and then transferred to another portion of the same animal (e.g., a brain of the same animal), and/or (e) any combination of the foregoing.

The term "transferring" as used herein can refer to adding fluids, cells, tissues, and/or organs to an animal and can refer to removing cells, tissues, and/or organs from an animal and replacing them with cells, tissues, and/or organs from another source. For example, neuronal tissue from a cloned porcine organism can be grafted into an appropriate area in the nervous system of a human to treat neurological diseases (e.g., Alzheimer's disease). In another example, a heart or part of a heart may be removed from a cloned porcine animal and can be surgically inserted into a human from which a heart or part of the heart was previously removed. Surgical methods for accomplishing this preferred aspect of the invention are known to a person of ordinary skill in the surgical arts. Transferring procedures may include the step of removing cells, tissues, fluids and/or organs from a recipient organism before a transfer step.

In other aspects the invention features (1) a cloned porcine animal prepared by a process comprising the steps of: (a) preparation of a cloned porcine embryo by any one of the methods described herein for producing such a cloned porcine embryo, and (b) manipulation of the cloned porcine embryo such that it develops into a live born animal; and (2) a process for cloning a porcine animal, comprising the steps of: (a) preparation of a cloned porcine embryo by any one of the methods described herein for preparing such a cloned porcine embryo, and (b) manipulation of the cloned mammalian embryo such that it develops into a live born porcine animal.

In preferred embodiments (1) the manipulation can comprise the step of implanting the embryo into a uterus of an animal; (2) the estrus cycle of the animal can be synchronized to the developmental stage of the embryo; and (3) the manipulation can comprise the step of implanting the embryo into an artificial environment.

In another aspect the invention features a process for cloning a porcine animal, comprising the steps of (a) translocation of a nuclear donor into an oocyte to establish a nuclear transfer oocyte; (b) non-electrical activation of the nuclear transfer oocyte to establish a cloned porcine embryo; and (c) transferring the porcine embryo into a recipient female, where the porcine embryo develops into a cloned porcine animal.

In preferred embodiments, (1) the nuclear donor is a cultured cell and is selected from any of the cell types described herein; (2) the nuclear donor is a totipotent cell; (3) translocation comprises fusion; and (4) the method comprises the step of culturing the porcine embryo in vitro. Any other preferred embodiments discussed herein with respect to porcine embryos, and especially with regard to activation, pertains to this aspect of the invention.

The summary of the invention described above is not limiting and other features and advantages of the invention will be apparent from the following detailed description of the preferred embodiments, as well as from the claims.

DETAILED DESCRIPTION OF THE PREFERRED EMBODIMENTS

Figure 1:
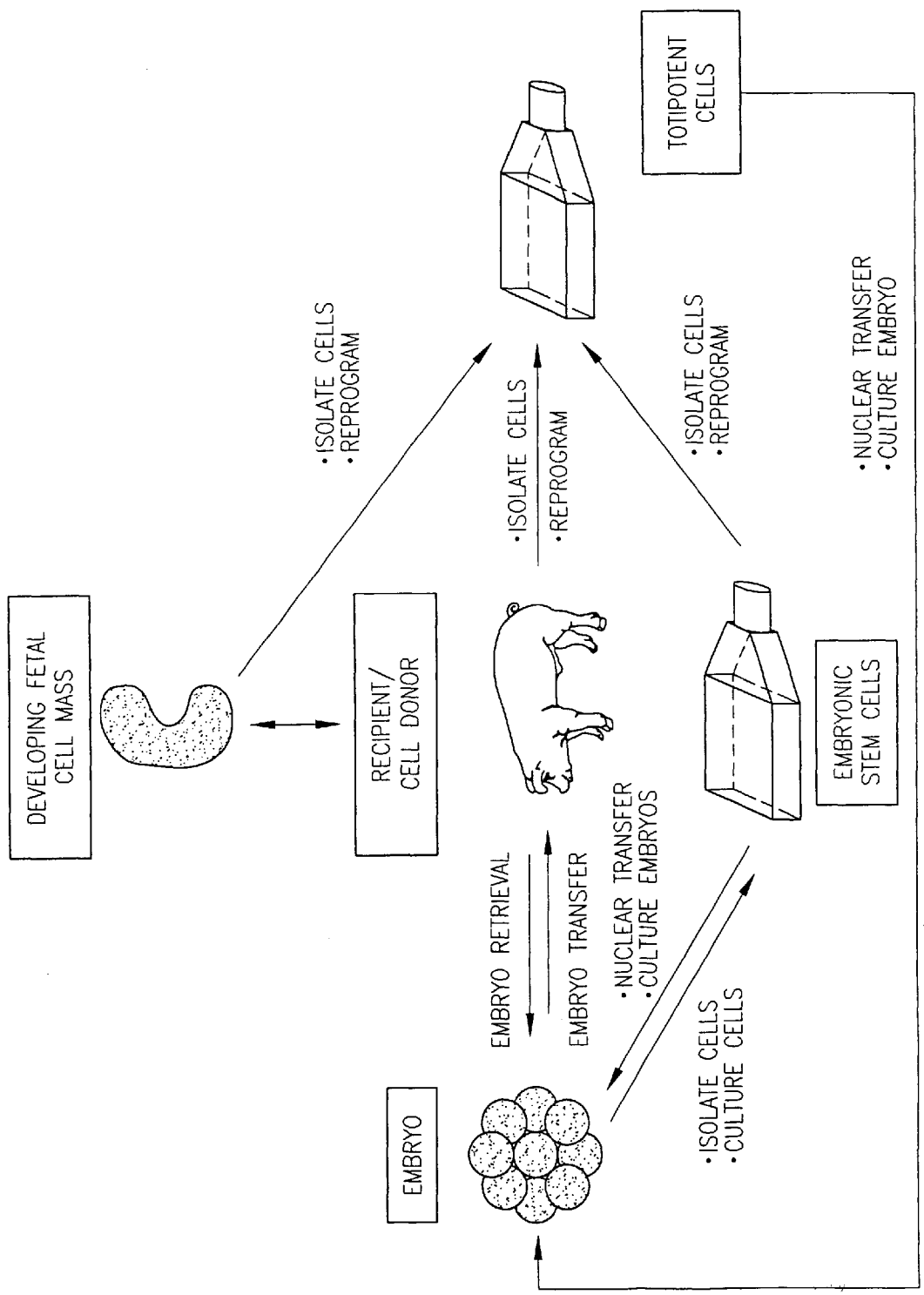
FIG. 1 illustrates multiple embodiments of the invention relating to the generation of totipotent cells from precursor cells. The figure indicates that totipotent cells can arise from embryonic stem cells, primordial germ cells, and cells isolated from an animal. The precursor cell sources illustrated by FIG. 1 are not limiting and other precursor cell sources are described herein.
Figure 2:
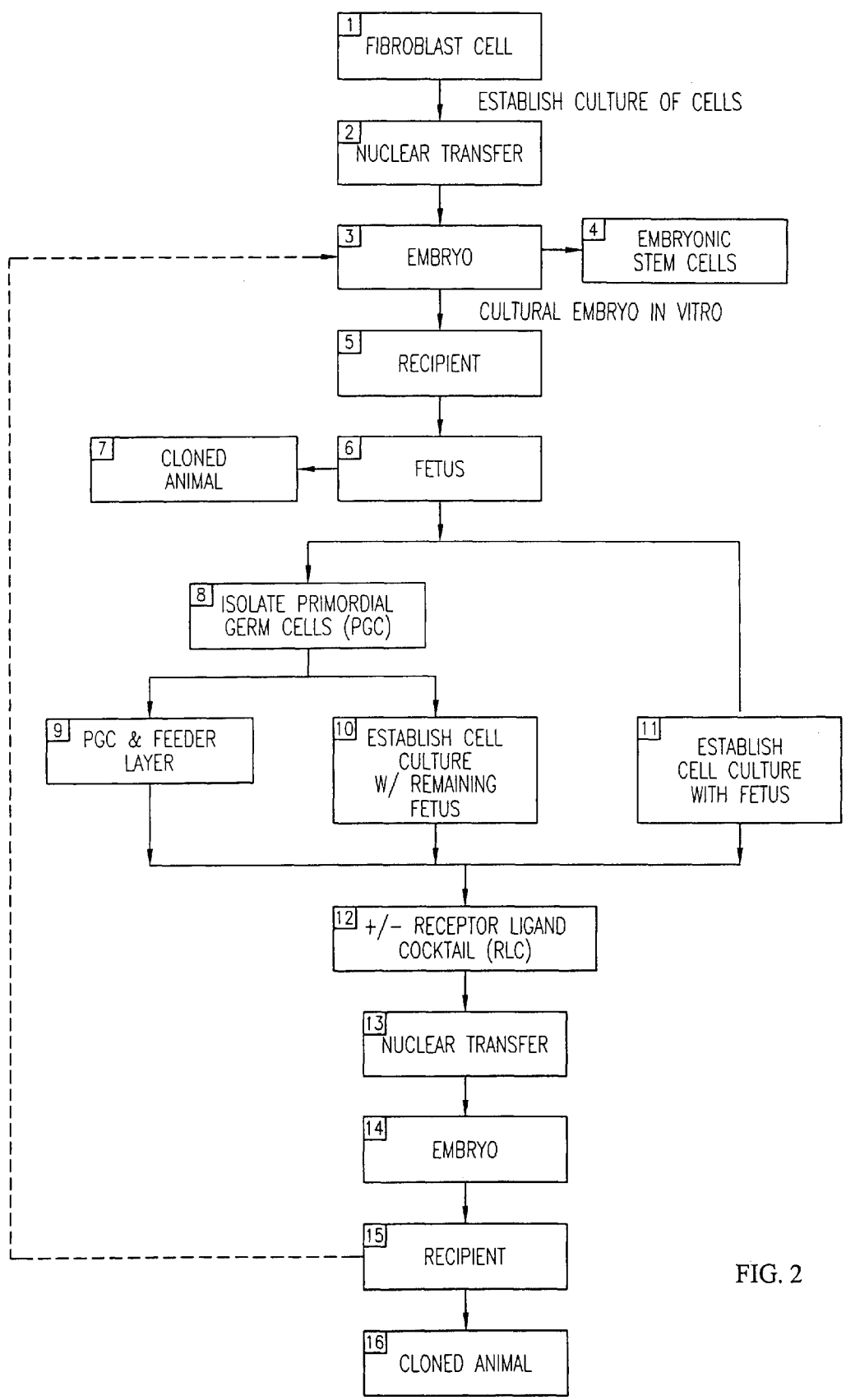
FIG. 2 illustrates multiple embodiments of the invention related to pathways for establishing totipotent cell lines and cloned animals. Fibroblast cells can be isolated from any source described herein.

The present invention relates to cloning technologies related to porcine animals. The present invention provides multiple advantages over tools and methods currently utilized in the field of cloning porcine animals. For example, the invention relates in part to totipotent cells useful for cloning porcine animals. These totipotent cells can give rise to methods of producing cloned porcine animals by utilizing virtually any type of cell. For example, cells isolated from a live born animal can be reprogrammed into totipotent cells. This feature of the invention provides an ability to assess a phenotype of an existing porcine animal and then readily establish a totipotent cell line for cloning that animal.

In addition, totipotent cells of the invention allow for establishing cell lines from virtually any type of cell. This reprogramming method is described previously herein. These totipotent cell lines offer a nearly unlimited source of donor cells for nuclear transfer cloning techniques. Moreover, this feature provides the advantage of enhancing cloning efficiency due to the lower differentiation rates of these cell lines than existing cell lines used for cloning. For example, embryonic stem cell lines can harbor multiple colonies of cells that are not totipotent. Cell lines of the invention can harbor a high percentage of totipotent cells.

Moreover, methods and processes for establishing totipotent cells, totipotent cloned embryos, and cloned animals of the invention enhance cloning efficiency. This enhanced efficiency satisfies a long felt need in the art.

I. Totipotent Porcine Cells

A. Establishing Totipotent Cells

Totipotent cells of the invention can be produced from virtually any type of precursor cell. Preferred embodiments of the invention relate to the following types of precursor cells: (1) embryos arising from the union of two gametes in vitro or in vivo; (2) embryonic stem cells (ES cells) arising from cultured embryonic cells (e.g., pre-blastocyst cells and inner cell mass cells); (3) cultured and non-cultured inner cell mass cells isolated from of embryos; (4) cultured and non-cultured pre-blastocyst cells; (5) cultured and non-cultured fetal cells; (6) cultured and non-cultured primordial germ cells; (7) cultured embryonic germ cells (EG cells) as they are defined herein; (8) cultured and non-cultured cells isolated from an animal; (9) cultured and non-cultured cumulus cells; (10) cultured and non-cultured amniotic cells; (11) cultured and non-cultured fetal fibroblast cells; (12) cultured and non-cultured genital ridge cells; (13) cultured and non-cultured differentiated cells; and (14) cultured and non-cultured non-differentiated cells or undifferentiated cells.

Totipotent cells of the invention are preferably generated from precursor cells specified herein. Cells derived from a porcine animal can be isolated from nearly any type of tissue. For example, an ear-punch can be taken from a porcine animal, cells from the sample can be dissociated, and dissociated cells can be subsequently cultured in vitro by using cell culture techniques well known to a person of ordinary skill in the art. Examples of materials and methods for culturing primary culture cells into totipotent cells are described in exemplary embodiments hereafter.

A variety of methods for culturing cells exist in the art. See, e.g., *Culture of animal cells: a manual of basic technique* (2nd. edition), Freshney, copyright 1987, Alan R. Liss, Inc., New York. Particularly, cells that are precursor cells for totipotent cells, as well as totipotent cells themselves, can be grown on feeder layers. Examples of feeder layers are well known to a person of ordinary skill in the art, and can arise from a number of different cells that are cultured in vitro. See, e.g., exemplary embodiment described hereafter and Strelchenko, 1996, *Theriogenology* 45: 130–141; Piedrahita et al., 1990, *Theriogenology* 34: 879–901; Piedrahita et al., 1998, *Biol. Reprod*. 58: 1321–1329; and Shim et al., 1997, *Theriogenology* 47: 245, each of which is incorporated herein by reference in its entirety including all figures, tables, and drawings. However, precursor cells for totipotent cells as well as totipotent cells themselves need not be grown on feeder layers.

A preferred culturing condition for these precursor cells is a cell culture medium that contains a significant amount of glucose, in an amount specified herein. The cell culture condition may contain a carbohydrate that differs from glucose and may also contain multiple types of carbohydrates and complex carbohydrates. A wide variety of carbohydrates are well known to a person of ordinary skill in the art. See, e.g., Sigma and DIFCO catalogs.

Preferred cell culture conditions also relate to cell culture media that include one or more antibiotics. Antibiotics suitable for use in cell culture media are well known in the art. See, e.g., *Culture of Animal Cells: a manual of basic techniques* (3$^{rd}$ edition), 1994, Freshney (ed.), Wiley-Liss, Inc.; *Cells: a laboratory manual* (vol. 1), 1998), Spector, Goldman, Leinwand (eds.), Cold Spring Harbor Laboratory Press; and *Animal Cells: culture and media*, 1994, Darling & Morgan, John Wiley and Sons, Ltd., each of which is incorporated herein by reference in its entirety including all figures, tables, and drawings.

Another example of a cell culture condition is a cell culture medium that contains one or more receptor ligands. Examples of receptor ligands are well known to a person of ordinary skill in the art. Cytokines and/or growth factors are preferred receptor ligands of the invention. See, e.g., R&D Systems Catalog, 614 McKinley Place N.E., Minneapolis, Minn. 55413. In exemplary embodiments, varying amounts of human recombinant leukemia inhibitory factor (hrLIF) and basic bovine fibroblast growth factor (bFGF) can be added to the culture medium to reprogram the precursor cells into totipotent cells. Varying concentrations of these two cytokines can be added to the culture medium, preferably in concentrations of 1–1000 ng/mL, more preferably in concentrations between 10–500 ng/mL, and most preferably about 100 ng/mL. Exogenous soluble and membrane-associated forms of steel factor are not required for converting precursor cells into totipotent cells.

These examples are not meant to be limiting and any cytokine or combination of cytokines can be added or deleted from those described in exemplary embodiments described hereafter. Preferred cytokines for generating totipotent cells can be selected from the group consisting of fibroblast growth factor (FGF), leukemia inhibitor factor (LIF), cardiotrophin 1 (CT-1), ciliary neurotrophic factor (CNTF), stem cell factor (SCF), oncostatin M (OSM), and any member of the interleukin (IL) family, including IL-6, IL-11, and IL-12.

Other cytokines and other molecules besides cytokines can be added or deleted from the receptor ligand cocktail described in the exemplary embodiments described hereafter to establish totipotent cells from any of the cells described in the previous paragraph. Any of the conditions for generating totipotent cells can be modified from those described herein. The ability of these modified conditions to generate totipotent cells can be monitored by methods defined in the section "Identification Totipotent Cells" described hereafter.

B. Identifying Totipotent Cells

Totipotent cells can be identified in a number of manners. Examples of tests for cell totipotency include:

(1) identifying a marker specific for totipotent cells;
(2) performing one or more nuclear transfer cycles with a cell (as described hereafter) and developing the resulting embryo into an animal.

Markers can be utilized to distinguish totipotent cells from non-totipotent cells. Markers can be selected from the group of low molecular weight markers, macromolecular markers, cell surface markers, and intracellular markers. Examples of markers that may be suitable for identifying totipotent cells can be selected from the group consisting of alkaline phosphatase, cytokeratin, vimentin, laminin, and c-kit. These markers are well known to a person of ordinary skill in the art and these examples are not meant to be limiting.

Some of these markers have been tested for cultured bovine cells being identified for totipotency. As noted previously, totipotent porcine cells of the invention may not appreciably stain for alkaline phosphatase. Therefore the cells of the invention are to be contrasted with pluripotent cells discussed in previously referenced publications. It should be noted that some of the exemplary markers listed previously may not be specific for totipotent cells as some of these markers may exist in pluripotent cells as well as in totipotent cells.

The invention relates to any markers specific for totipotent cells that are known to a person of ordinary skill in the art. Markers for totipotency that are not clearly defined in the art can be elucidated by processes such as differential display and genomics methods for elucidating totipotent cell markers. Totipotent cells may also be identified by subjecting cells to analysis of nucleic acid sequence content (e.g., hybridization techniques with nucleic acid probes). Nucleic acid samples from totipotent cells and nucleic acid samples from non-totipotent cells can be screened for particular nucleic acid sequences. If samples from non-totipotent cells lack a nucleic acid sequence present in totipotent cells, then this nucleic acid sequence could be a marker for distinguishing totipotent cells from non-totipotent cells. Similarly, if samples from non-totipotent cells harbor a nucleic acid sequence that totipotent cells lack, this nucleic acid sequence could be a marker for distinguishing totipotent cells from non-totipotent cells. Similar methods can elucidate polypeptide markers by utilizing polypeptide analytical techniques (e.g., PAGE, SDS-PAGE, procedures comprising antibodies, and HPLC techniques known in the art).

A preferred test for cell totipotency is determining whether cells give rise to totipotent embryos and eventually cloned animals. This test represents a definitive test for cellular totipotency. An example of such a test includes the following steps: (1) utilizing a potentially totipotent cell for nuclear transfer with an enucleated oocyte; (2) allowing the resulting cybrid to develop; (3) separating an embryo that developed from the cybrid into individual cells and subjecting one or more of the individual cells to a second round of nuclear transfer; (4) allowing a resulting cybrid from step (3) to develop into an embryo; (5) implanting the embryo from step (2) or (4) into a uterine environment; and (6) allowing the embryo to develop. If the ensuing fetus develops past the first trimester of pregnancy then the cells initially used for nuclear transfer are most likely totipotent cells. If the cells utilized for nuclear transfer develop into a live born cloned animal then the cells are definitively totipotent. Examples of the techniques utilized for this exemplary test (e.g., enucleation of oocytes and nuclear transfer) are described completely in the art and in exemplary embodiments defined hereafter.

Using the tests for identifying totipotent cells, the materials and described herein can be modified by a person of ordinary skill in the art to produce totipotent cells from any type of precursor cell. Hence, the invention covers any of the materials and methods described herein as well as modifications to these methods for generating totipotent cells, since a person of ordinary skill in the art can readily produce totipotent cells by utilizing the materials and methods described herein in conjunction with methods for identifying totipotent cells.

C. Identifying Totipotent Cells that are Permanent Cells

The materials and methods described above (e.g., culturing the cells with cytokines) may convert non-permanent cells into permanent cells. Other methods exist in the art for generating permanent cell lines from primary cells and for identifying permanent cells. For example, manipulating the activity of telomerase within the cells can immortalize cells. See, e.g., U.S. Pat. No. 5,645,986, entitled "Therapy and Diagnosis of Conditions Related to Telomere Length and/or Telomerase Activity," West et al., issued Jul. 8, 1997, and hereby incorporated by reference herein in its entirety including all figures, drawings, and tables.

Permanent cells can be identified by determining a number of times that cultured cells undergo cell division and double in cell numbers before the cells terminate. As discussed above, permanent cells may double over 10 times, 20 times, 30 times, 40 times, 50 times, and 60 times before the cells terminate. Materials and methods for measuring cell termination are taught above.

In addition, permanent cells can be identified by detecting the presence and/or absence of low molecular weight and macromolecular markers that are specific for permanent cells. The presence or lack of existence of a marker can be a determination of cell immortalization. In addition, a phenomenon associated with a marker can be an indication of immortality. For example, if the marker is an enzyme, an indication of the presence of the enzyme and/or a certain level of catalytic activity of that enzyme may be a suitable indication that a certain cell is permanent.

Low molecular weight markers include specific nucleosides, lipid associated sialic acids, polyamines, and pseudouridine. These examples are not limiting and the invention relates to any other low molecular weight markers known in the art.

Macromolecular markers can be separated into several classes including nucleic acid polymers, peptides, polypeptides, proteins, enzymes, growth factors, growth factor receptors, hormones, hormone receptors, oncogenes, oncogene products, and specific glycoproteins. Macromolecular markers can be selected from the group consisting of extracellular proteins, membrane associated proteins, and/or intracellular proteins, which may be membrane associated or soluble. One such marker for permanent cells is telomerase or its associated activity, for example. See, U.S. Pat. No. 5,645,986, supra. Other examples of markers specific for permanent cells can be selected from the following list. These examples are not limiting and the invention relates to any markers specific for permanent cells that are known in the art.

1) Epidermal growth factor (EGF) and its receptor (EGF-R)
2) Transforming growth factor-alpha (TGF-alpha) and its receptor
3) c-erbB2 receptor tyrosine kinase (HER2 product)
4) Hyaluronan receptor (probably CD44, an integral membrane glycoprotein)
5) Carcinoembryonic antigen (CEA) family of tumor markers (for example T1, a glycosylated protein)
6) Telomerase, a ribonucleoprotein which maintains telomere length in permanent cells
7) Phosphatases: placental alkaline phosphatase (PLAP), germ cell alkaline phosphatase, prostate acid phosphatase (PAS)
8) Cathepsin D (catalyzes degradation of laminin).
9) Ornithine decarboxylase (ODC) (catalyzes the rate-limiting step in polyamine synthesis)
10) Beta-glucuronidase
11) Alpha-6 integrin
12) Keratin K8
13) Oncogene products: ras oncogenes (k-ras, Ha-ras, p21), v-src, c-myc
14) Cyclin D1, cyclin A, and Retinoblastoma Gene Protein (Rb)
15) Changes in p53 expression or p53 mutations
16) Heterogeneous ribonucleoprotein-A2 (hnRNP-A2) over-expression
17) L-plastin
18) Ganglioside fucosyl-GM1
19) Mob-1 expression (mob-1) (homology to proinflammatory cytokines)

In addition to markers for cell permanence known in the art, markers for cell permanence can be identified using other methods well known in the art. For example, cell permanence markers can be identified by analyzing particular molecules (e.g., nucleic acid molecules and polypeptide molecules) that are unique to specific permanent cell types.

II. Transgenic Totipotent Porcine Cells

Materials and methods readily available to a person of ordinary skill in the art can be utilized to convert totipotent porcine cells of the invention into transgenic cells that are concomitantly totipotent. Once the nuclear DNA is modified in the totipotent cells of the invention, embryos and animals arising from these cells can lso comprise the modified nuclear DNA. Hence, materials and methods readily available to a person of ordinary skill in the art can be applied to the totipotent cells of the invention to produce transgenic animals and chimeric animals. See, e.g., EPO 264 166, entitled "Transgenic Animals Secreting Desired Proteins Into Milk"; WO 94/19935, entitled "Isolation of Components of Interest From Milk"; WO 93/22432, entitled "Method for Identifying Transgenic Pre-implantation Embryos"; WO 95/17085, entitled "Transgenic Production of Antibodies in Milk;" Hammer et al., 1985, *Nature* 315: 680–685; Miller et al., 1986, *J. Endocrinology* 120: 481–488; Williams et al., 1992, *J. Ani. Sci.* 70: 2207–2111; Piedrahita et al., 1998, *Biol. Reprod.* 58. 1321–1329; Piedrahita et al., 1997, *J. Reprod. Fert.* (*suppl.*) 52: 245–254;

and Nottle et al, 1997, *J. Reprod. Fert.* (*suppl.*) 52: 245–254, each of which is incorporated herein by reference in its entirety including all figures, drawings and tables.

Methods for generating transgenic cells typically include the steps of (1) assembling a suitable DNA construct useful for inserting a specific DNA sequence into the nuclear genome of a cell; (2) transfecting the DNA construct into the cells; (3) allowing random insertion and/or homologous recombination to occur. The modification resulting from this process may be the insertion of a suitable DNA construct(s) into the target genome; deletion of DNA from the target genome; and/or mutation of the target genome.

DNA constructs can comprise a gene of interest as well as a variety of elements including regulatory promoters, insulators, enhancers, and repressors as well as elements for ribosomal binding to the RNA transcribed from the DNA construct. DNA constructs can also encode ribozymes and anti-sense DNA and/or RNA, identified previously herein. These examples are well known to a person of ordinary skill in the art and are not meant to be limiting.

Due to the effective recombinant DNA techniques available in conjunction with DNA sequences for regulatory elements and genes readily available in data bases and the commercial sector, a person of ordinary skill in the art can readily generate a DNA construct appropriate for establishing transgenic cells using the materials and methods described herein.

Transfection techniques are well known to a person of ordinary skill in the art and materials and methods for carrying out transfection of DNA constructs into cells are commercially available. For example, materials that can be used to transfect cells with DNA constructs are lipophillic compounds, such as Lipofectin™, Superfect™, LipoTAXI™, and CLONfectin™. Particular lipophillic compounds can be induced to form liposomes for mediating transfection of the DNA construct into the cells. In addition, cationic based transfection agents that are known in the art can be utilized to transfect cells with nucleic acid molecules (e.g., calcium phosphate precipitation). Also, electroporation techniques known in the art can be utilized to translocated nucleic acid molecules into cells. Furthermore, particle bombardment techniques known in the art can be utilized to introduce exogenous DNA into cells. Target sequences from a DNA construct can be inserted into specific regions of the nuclear genome by rational design of the DNA construct. These design techniques and methods are well known to a person of ordinary skill in the art. See, U.S. Pat. No. 5,633,067, "Method of Producing a Transgenic Bovine or Transgenic Bovine Embryo," DeBoer et al., issued May 27, 1997; U.S. Pat. No. 5,612,205, "Homologous Recombination in Mammalian Cells," Kay et al., issued Mar. 18, 1997; and PCT publication WO 93/22432, "Method for Identifying Transgenic Pre-Implantation Embryos," each of which is incorporated herein by reference in its entirety entirety, including all figures, drawings, and tables. Once the desired DNA sequence is inserted into the nuclear genome of a cell, the location of the insertion region as well as the frequency with which the desired DNA sequence has inserted into the nuclear genome can be identified by methods well known to those skilled in the art.

Once a transgene or transgenes are inserted into the nuclear genome of the totipotent cell, that cell can be used as a nuclear donor for cloning a transgenic animal. A description of the embodiments related to transgenic animals are described in further detail hereafter.

A. Diseases and Parasites

Desired DNA sequences can be inserted into nuclear DNA of a cell to enhance the resistance of a cloned transgenic animal to particular parasites, diseases, and infectious agents. Examples of parasites include worms, flies, ticks, and fleas. Examples of infectious agents include bacteria, fungi, and viruses. Examples of diseases include Atrophic rhinitis, Cholera, Leptospirosis, Pseudorabies, and Brucellosis. These examples are not limiting and the invention relates to any disease or parasite or infectious agent known in the art. See, e.g., *Hagan & Bruners Infectious Dieseases of Domestic Animals* (7th edition), Gillespie & Timoney, copyright 1981, Cornell University Press, Ithaca N.Y.

A transgene can confer resistance to a particular parasite or disease by completely abrogating or partially alleviating the symptoms of the disease or parasitic condition, or by producing a protein which controls the parasite or disease.

B. Elements of DNA Constructs and Production of DNA Constructs

A wide variety of transcriptional and translational regulatory sequences may be employed, depending upon the nature of the host. The transcriptional and translational regulatory signals may be derived from viral sources, such as adenovirus, bovine papilloma virus, cytomegalovirus, simian virus, or the like, whereas the regulatory signals are associated with a particular gene sequence possessing potential for high levels of expression. Alternatively, promoters from mammalian expression products, such as actin, casein, alpha-lactalbumin, uroplakin, collagen, myosin, and the like, may be employed. Transcriptional regulatory signals may be selected which allow for repression or activation, so that expression of the gene product can be modulated. Of interest are regulatory signals which can be epressed or initiated by external factors such as chemicals or drugs. These xamples are not limiting and the invention relates to any regulatory elements. ther examples of regulatory elements are described herein.

C. Examples of Preferred Recombinant Products

A variety of proteins and polypeptides can be encoded by a gene harbored within a DNA construct suitable for creating transgenic cells. Those proteins or polypeptides include hormones, growth factors, enzymes, clotting factors, apolipoproteins, receptors, drugs, pharmaceuticals, bioceuticals, nutraceuticals, oncogenes, tumor antigens, tumor suppressors, cytokines, viral antigens, parasitic antigens, bacterial antigens and chemically synthesized polymers and polymers biosynthesized and/or modified by chemical, cellular and/or enzymatic processes. Specific examples of these compounds include proinsulin, insulin, growth hormone, androgen receptors, insulin-like growth factor I, insulin-like growth factor II, insulin growth factor binding proteins, epidermal growth factor, TGF-α, TGF-β, dermal growth factor (PDGF), angiogenesis factors (e.g., acidic fibroblast growth factor, basic fibroblast growth factor, and angiogenin), angiogenesis inhibitors (e.g., endostatin and angiostatin), matrix proteins (Type IV collagen, Type VII collagen, laminin), oncogenes (ras,fos, myc, erb, src, sis, jun), E6 or E7 transforming sequence, p53 protein, cytokine receptor, IL-1, IL-6, IL-8, IL-2, α, β, or γIFN, GMCSF, GCSF, viral capsid protein, and proteins from viral, bacterial and parasitic organisms. Other specific proteins or polypeptides which can be expressed include: phenylalanine hydroxylase, α-1-antitrypsin, cholesterol-7α-hydroxylase, truncated apolipoprotein B, lipoprotein lipase, apolipoprotein E, apolipoprotein A1, LDL receptor, scavenger receptor for oxidized lipoproteins, molecular variants of each, VEGF, and combinations thereof. Other examples are monoclonal antibodies, antibody fragments, clotting factors, apolipoproteins, drugs, tumor antigens, viral antigens, parasitic antigens, monoclonal antibodies, and bacterial antigens.

One skilled in the art readily appreciates that these proteins belong to a wide variety of classes of proteins, and that other proteins within these classes or outside of these classes can also be used. These are only examples and are not meant to be limiting in any way.

It should also be noted that the genetic material which is incorporated into the cells from DNA constructs includes (1) nucleic acid sequences not normally present in target cells; (2) nucleic acid molecules which are normally present in target cells but not expressed at physiological significant levels; (3) nucleic acid sequences normally present in target cells and normally expressed at physiological desired levels; (4) other nucleic acid sequences which can be modified for expression in target cells; and (5) any combination of the above.

In addition, DNA constructs may become incorporated into nuclear DNA of cells, where incorporated DNA can be transcribed into ribonucleic acid molecules that can cleave other RNA molecules at specific regions. Ribonucleic acid molecules which can cleave RNA molecules are referred to in the art as ribozymes. Ribozymes are themselves RNA molecules. Ribozymes can bind to discrete regions on a RNA molecule, and then specifically cleave a region within that binding region or adjacent to the binding region. Ribozyme techniques can thereby decrease the amount of polypeptide translated from formerly intact message RNA molecules.

Furthermore, DNA constructs can be incorporated into nuclear DNA of cells and when transcribed produce RNA that can bind to both specific RNA or DNA sequences. The nucleic acid sequences can be utilized in anti-sense techniques, which bind to the message (mRNA) and block the translation of these messages. Anti-sense techniques can thereby block or partially block the synthesis of particular polypeptides in cells.

III. Nuclear Transfer

Nuclear transfer (NT) techniques using non-totipotent cells are well known to a person of ordinary skill in the art. See, e.g., U.S. Pat. No. 4,664,097, "Nuclear Transplantation in the Mammalian Embryo by Microsurgery and Cell Fusion," issued May 12, 1987, McGrath & Solter; U.S. Pat. No. 4,994,384 (Prather et al.); and U.S. Pat. No. 5,057,420 (Massey et al.), each of which is incorporated herein by reference in its entirety, including all figures, tables, and drawings. Exemplary embodiments define a NT technique that may provide for efficient production of totipotent porcine embryos.

A. Nuclear Donors

Totipotent cells of the invention can be used as nuclear donors in a NT process for generating a cloned embryo. As described above, totipotent cells can be generated from nearly any type of cell. For NT techniques, a donor cell may be separated from a growing cell mass, isolated from a primary cell culture, or isolated from a cell line. The entire cell may be placed in the perivitelline space of a recipient oocyte or may be directly injected into the recipient oocyte by aspirating the nuclear donor into a needle, placing the needle into the recipient oocyte, releasing the nuclear donor and removing the needle without significantly disrupting the plasma membrane of the oocyte. Also, a nucleus (e.g., karyoplast) may be isolated from a nuclear donor and placed into the perivitelline space of a recipient oocyte or may be injected directly into a recipient oocyte, for example.

B. Recipient Oocytes

A recipient oocyte is typically an oocyte with a portion of its ooplasm removed, where the removed ooplasm comprises the oocyte nucleus. Enucleation techniques are well known to a person of ordinary skill in the art. See e.g., Nagashima et al., 1997, Mol. Reprod. Dev. 48: 339–343; Nagashima et al., 1992, J. Reprod. Dev. 38: 37–78; Prather et al., 1989, Biol. Reprod. 41: 414–418; Prather et al., 1990, J. Exp. Zool. 255: 355–358; Saito et al., 1992, Assis. Reprod. Tech. Andro. 259: 257–266; and Terlouw et al., 1992, Theriogenology 37: 309, each of which is incorporated herein by reference in its entirety including all figures, tables, and drawings.

Oocytes can be isolated from either oviducts and/or ovaries of live animals by oviductal recovery procedures or transvaginal oocyte recovery procedures well known in the art and described herein. Furthermore, oocytes can be isolated from deceased animals. For example, ovaries can be obtained from abattoirs and oocytes can be aspirated from these ovaries. The oocytes can also be isolated from the ovaries of a recently sacrificed animal or when the ovary has been frozen and/or thawed.

Oocytes can be matured in a variety of media well known to a person of ordinary skill in the art. One example of such a medium suitable for maturing oocytes is depicted in an exemplary embodiment described hereafter. Oocytes can be successfully matured in this type of medium within an environment comprising 5% $CO_2$ at 39° C. Oocytes may be cryopreserved and then thawed before placing the oocytes in maturation medium. Cryopreservation procedures for cells and embryos are well known in the art as discussed herein.

Components of an oocyte maturation medium can include molecules that arrest oocyte maturation. Examples of such components are 6-dimethylaminopurine (DMAP) and isobutylmethylxanthine (IBMX). IBMX has been reported to reversibly arrest oocytes, but the efficiencies of arrest maintenance are quite low. See, e.g., Rose-Hellkant and Bavister, 1996, Mol. Reprod. Develop. 44: 241–249. However, oocytes may be arrested at the germinal vesicle stage with a relatively high efficiency by incubating oocytes at 31° C. in an effective concentration of IBMX. Preferably, oocytes are incubated the entire time that oocytes are collected. Concentrations of IBMX suitable for oocyte maturation are 0.01 mM to 20 mM IBMX, preferably 0.05 mM to 10 mM IBMX, and more preferably about 0.1 mM IBMX to about 0.5 mM IBMX, and most preferably 0.1 mM IBMX to 0.5 mM IBMX.

A nuclear donor cell and a recipient oocyte can arise from the same specie or different species. For example, a totipotent porcine cell can be inserted into a porcine enucleated oocyte. Alternatively, a totipotent wild boar cell can be inserted into a domesticated porcine oocyte. Any nuclear donor/recipient oocyte combinations are envisioned by the invention. Preferably the nuclear donor and recipient oocyte from the same specie. Cross-species NT techniques can be utilized to produce cloned animals that are endangered or extinct.

Oocytes can be activated by electrical and/or non-electrical means before, during, and/or after a nuclear donor is introduced to recipient oocyte. For example, an oocyte can be placed in a medium containing one or more components suitable for non-electrical activation prior to fusion with a nuclear donor. Also, a cybrid can be placed in a medium containing one or more components suitable for nonelectrical activation. Activation processes are discussed in greater detail hereafter.

C. Injection/Fusion

A nuclear donor can be translocated into an oocyte using a variety of materials and methods that are well known to a person of ordinary skill in the art. In one example, a nuclear donor may be directly injected into a recipient oocyte. This direct injection can be accomplished by gently pulling a nuclear donor into a needle, piercing a recipient oocyte with that needle, releasing the nuclear donor into the oocyte, and removing the needle from the oocyte without significantly disrupting its membrane. Appropriate needles can be fashioned from glass capillary tubes, as defined in the art and specifically by publications incorporated herein by reference.

In another example, at least a portion of plasma membrane from a nuclear donor and recipient oocyte can be fused together by utilizing techniques well known to a person of ordinary skill in the art. See, Willadsen, 1986, *Nature* 320:63–65, hereby incorporated herein by reference in its entirety including all figures, tables, and drawings. Typically, lipid membranes can be fused together by electrical and chemical means, as defined previously and in other publications incorporated herein by reference.

Examples of non-electrical means of cell fusion involve incubating cybrids in solutions comprising polyethylene glycol (PEG), and/or Sendai virus. PEG molecules of a wide range of molecular weight can be utilized for cell fusion.

Processes for fusion that are not explicitly discussed herein can be determined without undue experimentation. For example, modifications to cell fusion techniques can be monitored for their efficiency by viewing the degree of cell fusion under a microscope. The resulting embryo can then be cloned and identified as a totipotent embryo by the same methods as those previously described herein for identifying totipotent cells, which can include tests for selectable markers and/or tests for developing an animal.

D. Activation

Methods of activating oocytes and cybrids are known to those of ordinary skill in the art. See, U.S. Pat. No. 5,496,720, "Parthenogenic Oocyte Activation," Susko-Parrish et al., issued on Mar. 5, 1996, hereby incorporated by reference herein in its entirety including all figures, tables, and drawings.

Both electrical and non-electrical processes can be used for activating cells (e.g., oocytes and cybrids). Although use of a non-electrical means for activation is not always necessary, non-electrical activation can enhance the developmental potential of cybrids, particularly when young oocytes are utilized as recipients.

Examples of electrical techniques for activating cells are well known in the art. See, WO 98/16630, published on Apr. 23, 1998, Piedraheidra and Blazer, hereby incorporated herein in its entirety including all figures, tables, and drawings, and U.S. Pat. Nos. 4,994,384 and 5,057,420. Non-electrical means for activating cells can include any method known in the art that increases the probability of cell division. Examples of non-electrical means for activating a nuclear donor and/or recipient can be accomplished by introducing cells to ethanol; inositol trisphosphate ($IP_3$); $Ca^{2+}$ ionophore and protein kinase inhibitors such as 6-dimethylaminopurine; temperature change; protein synthesis inhibitors (e.g., cyclohexamide); phorbol esters such as phorbol 12-myristate 13-acetate (PMA); mechanical techniques, thapsigargin, and sperm factors. Sperm factors can include any component of a sperm that enhance the probability for cell division. Other non-electrical methods for activation include subjecting the cell or cells to cold shock and/or mechanical stress.

Examples of preferred protein kinase inhibitors are protein kinase A, G, and C inhibitors such as 6-dimethylaminopurine (DMAP), staurosporin, 2-aminopurine, sphingosine. Tyrosine kinase inhibitors may also be utilized to activate cells.

Activation materials and methods that are not explicitly discussed herein can be identified by modifying the specified conditions defined in the exemplary protocols described hereafter and in U.S. Pat. No. 5,496,720.

Activation efficiency and totipotency that result from any modifications of activation procedures can be identified by methods described previously in the section entitled "Identification of Totipotent Cells." Methods for identifying totipotent embryos can include one or more tests, such as (a) identifying specific markers for totipotent cells in embryos, and (b) by determining whether the embryos are totipotent by allowing them to develop into an animal. Therefore, the invention relates to any modifications to the activation procedures described herein even though these modifications may not be explicitly stated herein.

F. Manipulation of Embryos Resulting from Nuclear Transfer

An embryo resulting from a NT process can be manipulated in a variety of manners. The invention relates to cloned embryos that arise from at least one NT. Exemplary embodiments of the invention demonstrate that two or more NT procedures may enhance the efficiency for the production of totipotent embryos. Exemplary embodiments indicate that incorporating two or more NT procedures into methods for producing cloned totipotent embryos may enhance placental development. In addition, increasing the number of NT cycles involved in a process for producing totipotent embryos may represent a necessary factor for converting non-totipotent cells into totipotent cells. An effect of incorporating two or more NT cycles upon totipotency of resulting embryos is a surprising result, which was not previously identified or explored in the art.

Incorporating two or more NT cycles into methods for cloned totipotent embryos can provide further advantages. Incorporating multiple NT procedures into methods for establishing cloned totipotent embryos provides a method for multiplying the number of cloned totipotent embryos.

When multiple NT procedures are utilized for the formation of a cloned totipotent embryo, oocytes that have been matured for any period of time can be utilized as recipients in the first, second or subsequent NT procedures. For example, if a first NT and then a second NT are performed, the first NT can utilize an oocyte that has been matured for about 53 hours as a recipient and the second NT may utilize an oocyte that has been matured for less than about 53 hours as a recipient. Alternatively, the first NT may utilize an oocyte that has been matured for about 53 hours as a recipient and the second NT may utilize an oocyte that has been matured for greater than about 53 hours as a recipient for a two-cycle NT regime. In addition, both NT cycles may utilize oocytes that have been matured for about 53 hours as recipients, both NT cycles may utilize oocytes that have been matured for less than about 53 hours as recipients, and both NT cycles may utilize oocytes that have been matured for greater than about 53 hours as recipients in a two-cycle NT regime.

For NT techniques that incorporate two or more NT cycles, one or more of the NT cycles may be preceded, followed, and/or carried out simultaneously with an activation step. As defined previously herein, an activation step may be accomplished by electrical and/or non-electrical means as defined herein. Exemplified embodiments described hereafter describe NT techniques that incorporate an activation step after one NT cycle. However, an activation step may also be carried out at the same time as a NT cycle (e.g., simultaneously with the NT cycle) and/or an activation step may be carried out prior to a NT cycle.

Cloned totipotent embryos resulting from a NT cycle can be (1) disaggregated or (2) allowed to develop further.

If embryos are disaggregated, disaggregated embryonic derived cells can be utilized to establish cultured cells. Any type of embryonic cell can be utilized to establish cultured cells. These cultured cells are sometimes referred to as embryonic stem cells or embryonic stem-like cells in the scientific literature. The embryonic stem cells can be derived from early embryos, morulae, and blastocyst stage embryos. Multiple methods are known to a person of ordinary skill in the art for producing cultured embryonic cells. These methods are enumerated in specific references previously incorporated by reference herein.

If embryos are allowed to develop into a fetus in utero, cells isolated from that developing fetus can be utilized to establish cultured cells. In preferred embodiments, primordial germ cells, genital ridge cells, and fetal fibroblast cells can be isolated from such a fetus. Cultured cells having a particular morphology that is described herein can be referred to as embryonic germ cells (EG cells). These cultured cells can be established by utilizing culture methods well known to a person of ordinary skill in the art. Such methods are enumerated in publications previously incorporated herein by reference and are discussed herein.

Cloned totipotent embryos resulting from NT can also be manipulated by cryopreserving and/or thawing the embryos. See, e.g., Nagashima et al., 1989, *Japanese J. Anim. Reprod.* 35: 130–134 and Feng et al., 1991, *Theriogenology* 35: 199, each of which is incorporated herein by reference in its entirety including all tables, figures, and drawings. Other embryo manipulation methods include in vitro culture processes; performing embryo transfer into a maternal recipient; disaggregating blastomeres for NT processes; disaggregating blastomeres or inner cell mass cells for establishing cell lines for use in NT procedures; embryo splitting procedures; embryo aggregating procedures; embryo sexing procedures; and embryo biopsying procedures. The exemplary manipulation procedures are not meant to be limiting and the invention relates to any embryo manipulation procedure known to a person of ordinary skill in the art.

IV. Development of Cloned Embryos

A. Identifying Totipotent Embryos

Totipotent embryos can be identified by the methods described in the section "Identification of Totipotent Cells." Individual cells can be isolated and subjected to similar tests. The tests relate to identifying the presence or absence of markers, for example. Also, a totipotent embryo can be identified by allowing an embryo to develop until it passes the first trimester of gestation, or preferably, develops into a live born animal. Methods for identifying markers for totipotency are also described herein.

B. Culture of Embryos In Vitro

Cloning procedures discussed herein provide an advantage of culturing cells and embryos in vitro prior to implantation into a recipient female. Methods for culturing embryos in vitro are well known to those skilled in the art. See, e.g., Nagashima et al., 1997, *Mol. Reprod. Dev.* 48: 339–343; Petters & Wells, 1993, *J. Reprod. Fert. (Suppl)* 48: 61–73; Reed et al., 1992, *Theriogenology* 37: 95–109; and Dobrinsky et al., 1996, *Biol. Reprod.* 55:1069–1074, each of which is incorporated herein by reference in its entirety, including all figures, tables, and drawings. In addition, exemplary embodiments for media suitable for culturing cloned embryos in vitro are described hereafter. Feeder cell layers may or may not be utilized for culturing cloned embryos in vitro. Feeder cells are described previously and in exemplary embodiments hereafter.

C. Development of Embryos In Utero

Cloned embryos can be cultured in an artificial or natural uterine environment after NT procedures and embryo in vitro culture processes. Examples of artificial development environments are being developed and some are known to those skilled in the art. Components of the artificial environment can be modified, for example, by altering the amount of a component or components and by monitoring the growth rate of an embryo.

Methods for implanting embryos into the uterus of an animal are also well known in the art, as discussed previously. Preferably, the developmental stage of the embryo(s) is correlated with the estrus cycle of the animal.

Embryos from one specie can be placed into the uterine environment of an animal from another specie. For example it has been shown in the art that bovine embryos can develop in the oviducts of sheep. Stice & Keefer, 1993, "Multiple generational bovine embryo cloning," *Biology of Reproduction* 48: 715–719. The invention relates to any combination of a porcine embryo in any other ungulate uterine environment. A cross-species in utero development regime can allow for efficient production of cloned animals of an endangered species. For example, a wild boar embryo can develop in the uterus of a domestic porcine sow.

Once an embryo is placed into the uterus of a recipient female, the embryo can develop to term. Alternatively, an embryo can be allowed to develop in the uterus and then can be removed at a chosen time. Surgical methods are well known in the art for removing fetuses from uteri before they are born.

V. Cloned Porcine Animals

As described previously herein, the invention provides advantages of being able to assess a phenotype of an animal before cloning that animal. Multiple products can be isolated from a cloned animal. For example, semen can be collected from a porcine animal, such as a domestic boar. Semen can be cryopreserved. Semen can also be separated into sex-specific fractions of sperm. See, U.S. Pat. Nos. 5,439,362, 5,346,990, and 5,021,244, entitled "Sex-associated Membrane Proteins and Methods for Increasing the Probability that Offspring Will be of a Desired Sex," Spaulding, and issued on Aug. 8, 1995, Sep. 13, 1994, and Jun. 4, 1991, respectively, each of which is incorporated herein by reference in its entirety including all figures, drawings, and tables. Methods of collecting semen are well known to a person of ordinary skill in the art, as discussed previously.

In addition, the invention relates in part to any products collected from a cloned porcine animal. The products can be any body fluids or organs isolated from the animal, or any products isolated from the fluids or organs. In preferred embodiments, products such as meat may be collected from cloned porcine animals. In another embodiment, the invention relates to determining the phenotype of a porcine animal, which is a neutered animal, and then cloning this animal such that the cloned animals are reproductively functional and can be used to produce semen. Other preferred embodiments of the invention relate to such products as xenograft materials, sperm, embryos, oocytes, any type of cells, and offspring harvested from cloned animals of the invention.

Xenograft materials, which are described previously herein, can relate to any cellular material extracted from one organism and placed into another organism. Medical procedures for extracting the cellular material from one organism and grafting it into another organism are well known to a person of ordinary skill in the art. Examples of preferable xenograft cellular materials can be selected from the group consisting of liver, lung, heart, nerve, gallbladder, and pancreas cellular material.

As discussed in a previous section, transgenic animals can be generated from the methods of the invention by using transgenic techniques well known to those of ordinary skill in the art. Preferably, cloned transgenic porcine animals are produced from these methods. These cloned transgenic animals can be engineered such that they are resistant or partially resistant to diseases and parasites endemic to such animals. Examples of these diseases and parasites are outlined in a preceding section.

Moreover, the cloned transgenic animals can be engineered such that they produce a recombinant product. Examples of recombinant products are outlined in a preceding section. The expression of these products can be directed to particular cells or regions within the cloned transgenic animals by selectively engineering a suitable promoter element and other regulatory elements to achieve this end.

For example, human recombinant products can be expressed in the urine of cattle by operably linking a uroplakin promoter to the DNA sequence encoding a recombinant product. Alternatively, examples are well known to a person of ordinary skill in the art for selectively expressing human recombinant products in the milk of a bovine animal.

Once the recombinant product or products have been expressed in a particular tissue or fluid of the cloned transgenic animal, the suitable tissue or fluid can be collected using methods well known in the art. Recombinant products can be purified from that fluid or tissue by using standard purification techniques well known to a person of ordinary skill in the art.

EXAMPLES

The examples below are non-limiting and are merely representative of various aspects and features of the present invention.

Example 1
Feeder Layer Preparation

A fetal fibroblast feeder cell layer was prepared from mouse fetuses that were from 10 to 20 days gestation. The head, liver, heart and alimentary tract were removed and the remaining tissue washed and incubated at 37° C. in 0.05% trypsin and 0.53 mM EDTA (Gibco BRL catalog no. 15400–096). Loose cells were cultured in tissue culture dishes containing MEM-alpha supplemented with penicillin, streptomycin, 10% fetal calf serum and 0.1 mM 2-mercaptoethanol. The feeder cell cultures were established over a two to three week period at 37.4° C., 3.5% $CO_2$ and humidified air. Before being used as feeder cells, mouse fibroblasts were pre-treated with mitomycin C (Calbiochem catalog no. 47589) at a final concentration of 10 $\mu$g/ml for 3 hours and washed 5 times with PBS before pre-equilibrated growth media was added.

Feeder cells can be established from porcine fetuses as described hereafter for establishing cultured porcine fetal fibroblast cells.

Example 2
Establishing Cultured Nuclear Donor Cells From Non-Embryonic Tissue

One advantage provided by the materials and methods defined herein is the ability to establish a totipotent cell from virtually any type of precursor cell.

1. Establishing Cultured Cells from Porcine Fetal Tissue

Genital ridge cells were isolated from porcine fetuses and were dissociated with proteolytic enzymes (Pronase E or trypsin). Cells having EG cell morphology formed directly out of the genital ridge digests but grew more quickly when established on mouse feeder layers (see, Example 1). The addition of growth factors hrLIF and bFGF to cell culture media had little effect on EG cell establishment and proliferation. EG cell proliferation rates increased when 17 mM D-glucose was incorporated into culture media. Cell culture media contained alpha-MEM, 10% fetal bovine serum, and 0.1 mM 2-mercaptoethanol.

Fetuses of age 33, 36, 47 and 54 days were used as a source of genital ridge cells. EG cells from 33, 36 and 47 day old fetuses were more difficult to establish and generally grew slowly. EG cells were overgrown by other cell types, typically elongated cells which looked like fibroblasts, when cell cultures were established from genital ridge cells isolated from 33, 36 and 47 day old fetuses. In contrast, EG cells from a 54 day old fetus grew relatively quickly and formed large colonies within 1–2 weeks. EG cells were physically isolated from other competing cell types and were grown to confluence as a monolayer of one apparent cell type with a typical EG cell morphology, a morphology that is described herein.

2. Establishing Cultured Porcine Cumulus Cells

Cumulus cells were isolated from porcine cumulus-oocyte complexes matured in vitro. Cumulus-oocyte complexes were collected from slaughterhouse derived ovaries and matured in a porcine maturation medium (described hereafter). Cumulus cells were stripped from cumulus-oocyte complexes by placing the cumulus-oocyte complexes with 500 $\mu$L TL HEPES in 15 ml-centrifuge tubes and vortexing the contents of the tubes using a vortex mixer (vortexed 3 minutes at half speed).

A cell suspension resulting from the vortexed cumulus-oocyte complexes were transferred into a Petri dish after washing two times with 10 mL of TL HEPES. The Petri dish was placed under a microscope and oocytes were manually removed from the cell suspension with a small bore pipette.

Once oocytes were removed from the cell suspension, remaining cumulus cells were placed in a 15 mL centrifuge tube. The tube was placed in a centrifuge to pellet the cumulus cells. Pelleted cumulus cells were resuspended in 5 mL of culture media containing MEM-alpha, 10% fetal calf serum, 0.1 mM β-mercaptoethanol, and aliquoted into a 60 mm tissue culture dish at a cell density of approximately 25,000 cells/mL.

Cumulus cells were cultured using standard cell culture techniques. Cell culture media was changed every 3–4 days and cumulus cells were passaged when confluent.

3. Establishing Cultured Porcine Amniotic Cells

Amniotic fluid is collected from a pregnant porcine female using a guided needle technique. Amniotic fluid is transferred into 15 mL conical tubes and centrifuged at 1000×g for 10 minutes. Supernatant fluid is removed, leaving 1 mL of fluid on the cell pellet. The cell pellet is resuspended in that 1 mL of amniotic fluid. 0.5 mL of the amniotic cell sample is added to 4.5 ml of complete AmnioMax medium (90 mL of AmnioMax-C100 Basal medium +15 mL of AmnioMax-C100 supplement [Gibco BRL]) in a T25 culture flask and placed in an incubator having a temperature of 39° C. and an atmosphere containing 5% $CO_2$.

Amniotic cells attach to culture flasks within approximately four days. Amniotic cell cultures were typically 70% confluent within 7–14 days. Cells are passaged by removing cell culture medium from flasks and washing cells twice with EBSS media or PBS media (without calcium or magnesium, Gibco BRL). 0.2 ml of a Trypsin/EDTA solution (Gibco BRL) is added to culture flasks and incubated at 39° C. until cells released from culture flask surfaces. After cells release from culture flask surfaces, cell culture media is added to flasks to inactivate trypsin and cells were divided over three new T25 flasks.

4. Establishing Cultured Porcine Fetal Fibroblast Cells

Cultured porcine fetal fibroblast cells were prepared from porcine fetuses that were from 33 to 54 days gestation. The head, liver, heart and alimentary tract were removed and the remaining tissue washed and incubated at 37° C. in 0.05% trypsin and 0.53 mM EDTA (Gibco BRL Catalog No. 15400–096) diluted with Ca2+ and Mg2+ free Dulbecco's PBS (Gibco BRL Catalog No. 14190–151). Loose cells were cultured in tissue culture dishes containing MEM-alpha (Gibco BRL catalog no. 32561–037) supplemented with penicillin, streptomycin, 10% fetal bovine serum (Hyclone catalog no. SH30070.03), and 0.1 mM 2-mercaptoethanol (Gibco BRL catalog no. 21985–023). Porcine fetal cells were established over a two to three week period at 37.4° C., 3.5% $CO_2$ and humidified air.

5. Establishing Cultured Porcine Fibroblast Cells from Adult Animals

A first step towards establishing totipotent cells from tissues of grown animals is establishing a primary culture of isolated cells. Although the following procedure relates to ear punch samples, this procedure can apply to cells isolated from any type of tissue. The following steps are preferably performed utilizing sterile procedures:

1. Wash each ear sample twice with 2 mL of trypsin/EDTA solution in two separate 35 mm Petri dishes. Process each ear sample separately. Mince the ear sample with sterile scissors and scalpel in a 35 mm Petri dish containing 2 mL of trypsin/EDTA solution. The minced pieces are preferably less than 1 mm in diameter.
2. Incubate minced ear pieces in the trypsin/EDTA solution for 40–50 min. in a 37° C. incubator with occasional swirling. The trypsin/EDTA solution is described in more detail hereafter. The dish may be wrapped with a stretchable material, such as Parafilm®, to reduce $CO_2$ accumulation.
3. Transfer digested ear pieces to a 15 mL sterile tube. Wash the dish from which the digested ear pieces were recovered with 2 mL of the trypsin/EDTA solution and transfer this wash solution to the sterile tube.
4. Vortex the tube at high speed for 2 min.
5. Add 5 mL of cell culture media (defined below) to inactivate the trypsin.
6. Centrifuge the 15 mL tube at 280×g for 10 minutes.
7. Decant the supernatant and re-suspend the cell pellet in residual solution by gently taping the side of the tube.
8. Add 2 mL of cell culture media to the tube and then centrifuge as described in step 6.
9. Decant the supernatant, re-suspend the pellet as described in step (7), then add 2 mL of media.
10. Keep 2–3 pieces of the ear for DNA analysis and store at −80° C. in a 2 mL tube.
11. Transfer resuspended cells into a 35 mm culture dish and incubate at 37° C. in a humidified 5% $CO_2$/95% air atmosphere.
12. Change media every 2–4 days.

A trypsin/EDTA solution was prepared by mixing a trypsin-EDTA solution (Gibco BRL Catalog No. 15400–096) with $Ca^{2+}$-free and $Mg^{2+}$-free Dulbecco's phosphate-buffered saline (PBS) (Gibco BRL catalog no. 14190–151) such that the solution contained 0.05% trypsin (w/v) and 0.53 mM EDTA. The solution was sterilized by filtration through a 0.2 µm filter.

A cell culture medium was prepared by combining minimum essential MEM-alpha (Gibco BRL catalog no. 32561–037), 10% fetal bovine serum (Hyclone #SH30070.03), 0.1 mM 2-mercaptoethanol (Gibco BRL catalog no. 21985–023), 100 U/mL penicillin, 100 µg/mL streptomycin, 0.25 µg/mL amphotercin B (Fungizone).

Example 3

Reprogramming Cultured Porcine Cells

If cultured cells established by the processes taught in Example 2 are not clearly totipotent, cells can be reprogrammed by the following process.

A genital ridge cell suspension (final concentration 100,000 cells/ml) is placed into a 35 mm Petri dish containing a murine primary embryonic fibroblast feeder layer. Culture media can be minimum essential MEM-alpha (Gibco BRL catalog no. 32561–037), 10% fetal bovine serum (Hyclone catalog no. SH30070.03), 0.1 mM 2-mercaptoethanol (Gibco BRL catalog no. 21985–023), 100 ng/ml human recombinant leukemia inhibitory factor (hrLIF; R&D System catalog no. 250-L), 100 ng/ml bovine basic fibroblast growth factor (bFGF; R&D System catalog no. 133-FB) at 37.5° C. and 5% $CO_2$. Exogenous steel factor (e.g., membrane associated steel factor and soluble steel factor) need not be added to the culture media.

Culture medium supplemented with 100 ng/mL hrLIF and 100 ng/mL bFGF is typically incubated with precursor cells for ten to fourteen days. Supplemented medium is replaced with fresh supplemented medium every 2–4 days. At any time in this culture process, EG cells may be observed. These EG cells can be isolated from the cell culture and cultured separately to establish homogenous EG cell cultures.

To maintain EG cell lines, high density population cells are passaged every week at a dilution ratio of 1:4 to 1:8. Cells are passaged by incubating them with a 0.05% trypsin—0.53 mM EDTA mixture and preparing new cultures in fresh growth medium. The growth promoting capacity of MEM-alpha media for totipotent cells can be enhanced by adding insulin-transferrin, sodium selenite supplement, diluted to 1:100 (Sigma catalog no. 11884) to the cell culture media. As a preventive measure against mycoplasma contamination, short term cultivation with tylosine tartrate (Sigma catalog no. T3151) is carried out. Before NT, cell lines are tested for presence of mycoplasma by PCR performed with DNA primers specific for mycoplasma sequences (Stratagene catalog no. 302007).

Example 4

Oocyte Maturation

1. Oocyte Aspiration and Collection

Sow ovaries were transported to a laboratory at 25° C. and immediately ashed with 0.9% saline. Follicles between 3–6 mm are aspirated using 18 gauge needles and 50 mL tubes connected to a vacuum system, where the vacuum was adjusted for a flow rate of 45 mL/minute. Following aspiration, oocytes were allowed to settle for 5–10 minutes. Follicular fluid (pFF) was aspirated and saved for use in maturation systems, if needed.

Oocytes were washed by resuspending them in 20 mL Hepes-PVA medium and then allowing the oocytes to settle. The medium was removed and the washing step was repeated two more times. Hepes-PVA medium contains 114 mM NaCl, 3 mM KCL, 2 mM $CaCl_2$, 0.5 mM $MgCl_2$, 2 mM $NaHCO_3$, 0.3 mM $NaH_2PO_4$, 10 mM HEPES, 12 mM sorbitol, 0.2 mM sodium pyruvate, 005 µL/mL gentamycin, 0.07 grams/L penicillin G, 0.1 grams/L polyvinyl alcohol, and 2 mL/L sodium lactate and has a pH of 7.4. Washed oocytes were then placed into maturation media.

2. In Vitro Maturation

Oocytes were washed three times in maturation media and fifty oocytes/well were transferred to 0.5 mL of maturation media in 4 well plates for 20–22 hours, where the maturation media contained hormones. In addition, 6–8 follicle shell pieces were added to the wells, although the addition of the shell pieces is optional. These follicle shell pieces are known to improve cytoplasmic maturation of porcine oocytes, which results in an increase in the developmental potential of the oocyte. See, e.g., Abeydeera et al., 1998, *Biol. Reprod.* 58: 213–218.

Maturation media contained 109 mM NaCl, 5 mM KCl, 2 mM $CaCl_2$, 1 mM $MgSO_4$, 25 mM $NaHCO_3$, 1 mM $KH_2PO_4$, 6 mM glucose, 1 mM glutamine, 12 mM sorbitol, 5 mg/L insulin, 100 IU/L penicillin G, and 50 mg/L streptomycin and has a pH of 7.4. Porcine follicular fluid (pFF) can be added to the maturation media in a concentration of approximately 10% (volume to volume). Also, β-mercaptoethanol can be added to the maturation media to a final concentration of 50 µM. In addition, cysteine can be added to the maturation media to a final concentration of 0.6 mM. Maturation media with hormones contained 10 ng/mL epidermal growth factor, 10 U/mL equine chorionic gonadotropin, 10 U/mL human chorionic gonadotropin, and 1 mM db-cAMP.

The oocytes and follicle shell pieces were then transferred to 0.5 mL of fresh maturation media and matured for an additional 20–22 hours, where maturation media did not contain hormones or db-cAMP. Oocytes were matured for a total of 40–44 hours at 39° C. in 5.0% $CO_2$ atmosphere.

Example 5

Nuclear Transfer

After 42–46 hours of maturation, oocytes were stripped of cumulus cells by vortexing the matured oocytes for approximately 2 minutes. After vortexing, the oocytes were evaluated for polar body formation rates. Polar body formation rates can be evaluated by visual detection with a stereomicroscope. Visual evaluation of polar body formation rates can be enhanced by staining oocytes in a medium containing 3 µg/mL Hoechst 33342 and 7.5 µg/mL cytochalasin B for approximately 20 minutes. Oocytes were then enucleated with an enucleation pipette.

NT processes were performed after oocytes were enucleated. In each NT procedure, a nuclear donor cell was placed adjacent to an oocyte such that a portion of the plasma membrane for each cell touched one another and such that the nuclear donor was adjacent to the zona pellucida of the oocyte. Porcine EG cells, cultured porcine genital ridge cells, cultured porcine fibroblast cells, and cultured porcine cumulus cells, and cumulus cells that have been dissociated from a cumulus-oocyte complex following 48 hour maturation were used as nuclear donors for the NT processes.

After a nuclear donor was placed adjacent to an enucleated oocyte, the two cells were fused. Three media can be used for fusing the cells: (1) 0.25 M sorbitol, 0.1 mM CaOAc, 0.5 mM MgOAc, and 0.1% BSA; (2) 0.3 M mannitol, 0.1 mM $MgSO_4$, 0.5 mM $CaCl_2$, and 0.1% BSA; (3) 0.3 M mannitol, 5% TL Hepes, and 0.3% BSA; and (4) Zimmerman's medium. After fusion, the fused oocytes were placed in culture for 4 hours, where the culture contained 109 mM NaCl, 5 mM KCl, 2 mM CaCl2, 1 mM $MgSO_4$, 25 mM $NaHCO_3$, 1 mM $KH_2PO_4$, 6 mM glucose, 1 mM glutamine, 7 mM taurine, 5 mM hypotaurine, 0.4% BSA, 100 IU/L penicillin G, and 50 mg/L streptomycin and had a pH of 7.4. The fused oocytes can also be cultured in a CR2 medium (CR1 medium supplemented with amino acids), the latter of which is described in U.S. Pat. No. 5,096,822, "Bovine embryo medium," Rosenkrans Jr. et al., Nov. 3, 1992, hereby incorporated herein by reference in its entirety, including all figures, tables, and drawings.

Example 6

Activation

After being cultured for 4 hours after fusion, fused oocytes were incubated in 10 µM ionomycin in ZI solution (TL Hepes stock+1 mg/ml BSA) for 8 minutes and then rinsed in Z30 solution (TL Hepes stock+30 mg/ml BSA) for 5 minutes. TL Hepes stock contained 114 mM NaCl, 3 mM KCl, 2 mM $NaHCO_3$, 0.3 mM $NaH_2PO_4$, 10 mM Hepes, 2 mM $CaCl_2$, 0.5 mM $MgCl_2$, 2 ml/L sodium lactate, and 1 ml/L phenol red and has a pH of 7.4

Oocytes were washed 3 times with TL Hepes PVA and then placed in 2 mM DMAP solution in CR2 medium with BSA for 4 hrs at 39° C. in a 5.0% $CO_2$ atmosphere. Following activation, activated oocytes were rinsed three times with TL Hepes PVA and placed in porcine embryo culture media.

Example 7

In Vitro Culture of Activated Oocytes and Embryos

After removal from DMAP solution, activated oocytes and cybrids were washed 3 times in TL Hepes PVA and placed in porcine embryo culture media for 4 days. Embryo culture media contained 109 mM NaCl, 5 mM KCl, 2 mM $CaCl_2$, 1 mM $MgSO_4$, 25 mM $NaHCO_3$, 1 mM $KH_2PO_4$, 6 mM glucose, 1 mM glutamine, 12 mM sorbitol, 5 mg/L insulin, 100 IU/L penicillin G, and 50 mg/L streptomycin and has a pH of 7.4. Activated ooyctes and cybrids may also be cultured in CR2 medium. On day 4, embryos are evaluated for cleavage and transferred into fresh embryo culture media that is supplemented with 10% fetal calf serum (v/v) for an additional 3 days. On day 7 embryos are evaluated for development to blastocysts.

Example 8

Recloning Process

One or more optional recloning cycles can be employed for enhancing totipotency of nuclear donor cells. In a recloning cycle, embryos from a first NT cycle are disaggregated either by pronase E (1–3 mg/ml in TL HEPES) or mechanically after treatment with cytochalasin B, when the embryos are at the morula stage. Single blastomeres are placed into the perivitelline space of an enucleated oocyte (52–54 hours post maturation, as taught in Example 4).

A single blastomere is fused into the enucleated oocyte via electrofusion in a 500 µm chamber with an electrical pulse of 105V for 15µs in an isotonic sorbitol solution (0.25 M) at 30° C. It is not required that the fused oocyte is subject to chemical activation for recloning cycles.

After oocyte fusion, fused oocytes from the second NT cycle are cultured in embryo culture media under humidified air with 5% $CO_2$ at 39° C. Such embryos can be transferred into a recipient female.

Example 9

Transfer of Porcine Embryos into a Maternal Recipient and Development of a Cloned Porcine Animal Ten gilts are injected with gonadotrophins (PG600™), which should result in approximately 2–5 recipients displaying estrus 3–5 days post-treatment. Synchronized gilts will be utilized for embryo transfer either on day 3 or day 5 of estrus. Early stage embryos (<8 cells) are transferred into recipients on day 3 of estrus, and later stage embryos (>8 cells) are transferred into additional recipients on day 5 of estrus. Animals are anesthetized, a mid-ventral laparotomy performed and the reproductive tract exposed. The embryo transfer procedure consists of transferring 30–50 early stage embryos that will be deposited into the oviduct, or transferring later stage embryos (morula and/or blastocyst stage embryos) into the uterine horn. Recipients are evaluated for initiation of pregnancy and are continually monitored with weekly ultrasound exams.

Example 10

Cloning Transgenic Porcine Animals

Figure 3:
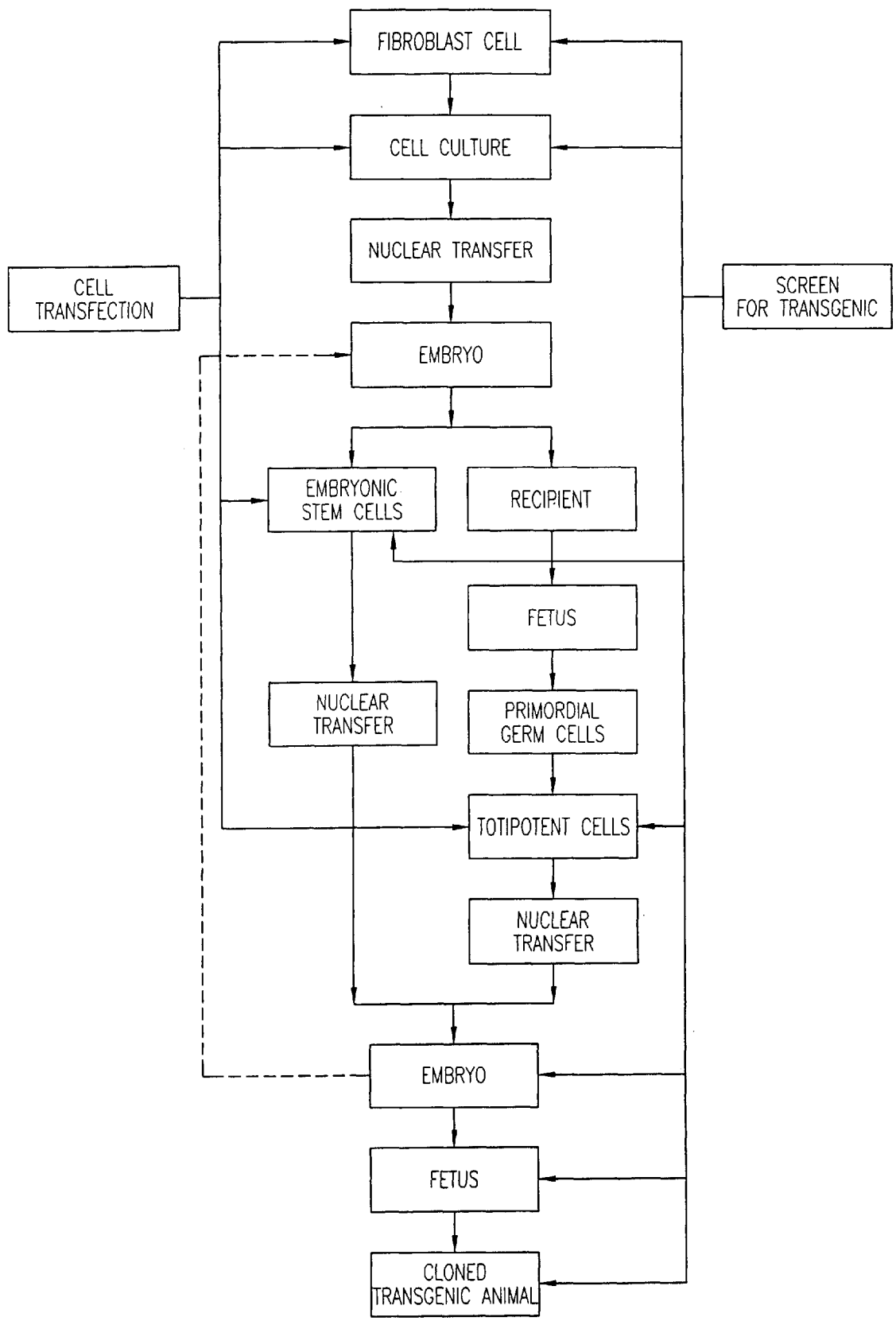
FIG. 3 illustrates multiple embodiments of the invention for establishing cloned transgenic cell lines and cloned transgenic animals.

Transgenic cells suitable for establishing a cloned transgenic porcine animal can be prepared from cells isolated from an adult animal. FIG. 3 illustrates processes that can be utilized to establish such transgenic cells. Although transgenic cells can be established from nearly any cell type by using the teachings of the invention, FIG. 3 illustrates procedures for establishing transgenic embryonic stem cells and transgenic totipotent cells.

Fibroblast cell cultures can be established from ear punches extracted from a porcine animal as defined previously. In addition, cultured fibroblast cells can be established from porcine fetuses. Individual cells can be isolated from this cell culture and utilized as nuclear donors in a nuclear transfer process. A single nuclear transfer cycle or multiple nuclear transfer cycles can be applied. Other optional steps are defined in previous examples.

Cells can then be transfected with a DNA construct. Cells can be transfected at multiple steps, as indicated in FIG. 3. Materials and methods for preparing transgenic cells are defined in publications referenced previously. Totipotent cells of the invention can be transfected with a DNA comprising (a) an antibiotic resistance gene; (b) a DNA sequence encoding a protein or proteins; and (c) a promoter element or elements. The transfected cells are selected for transgenic modification by selection in cell culture media containing antibiotic. The transgenic cells are then screened for transgenic modification by utilizing one or more screening techniques. Examples of these techniques are: (1) polymerase chain reaction, (2) Southern blotting, and (3) fiber-FISH procedures. These techniques are well known to a person of ordinary skill in the art. The latter two techniques can be utilized to determine the number of copies of an inserted gene sequence in embryonic germ cell nuclear DNA.

These screening procedures can be applied to transfected cells at any of the steps indicated in FIG. 3. Cloned transgenic animals are established by utilizing a transgenic cell as a nuclear donor in an NT process, as described in Example 5. Fused oocytes produced by such a process are subjected to the procedures taught in Examples 6, 7, and 9 and optionally 8 for the production of a cloned transgenic porcine animal.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The cell lines, embryos, animals, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

Other embodiments are set forth within the following claims.

What is claimed is:

1. A method for preparing a porcine embryo capable of developing into a live-born porcine animal, the method comprising:
   (a) obtaining a totipotent porcine nuclear donor cell from a cell culture;
   (b) forming a cybrid by translocating said totipotent porcine nuclear donor cell, or nucleus thereof, into an enucleated porcine oocyte, wherein prior to enucleation, said oocyte has been matured for between 42 and 56 hours, and before, during or after said translocation, activating said oocyte;
   (c) culturing said cybrid to establish said porcine embryo.

2. A method according to claim 1, wherein said porcine nuclear donor cell is a transgenic cell.

3. A method according to claim 1, further comprising cryopreserving said porcine embryo.

4. The method according to claim 1 wherein said forming of step (b) comprises:
   (i) fusing said cultured totipotent porcine nuclear donor cell and said enucleated oocyte to form a fused cell; and
   (ii) activating said fused cell.

5. A method according to claim 4, wherein said fusion of step (i) comprises using an electrical stimulus.

6. A method according to claim 4, wherein said activation of step (ii) comprises increasing intracellular levels of divalent cations and reducing phosphorylation of cellular proteins in said fused cell.

7. A method according to claim 6, wherein said activation of step (ii) comprises incubating said fused cybrid in a medium comprising ionomycin and/or 6-dimethylaminopurine.

8. A method according to claim 7, wherein said medium comprises ionomycin at a concentration of from 10 $\mu$M to 50 $\mu$M.

9. A method according to claim 1, wherein said totipotent porcine nuclear donor cell is a fetal cell.

10. A method according to claim 9, wherein said fetal cell is a somatic cell or a genital ridge cell.

11. A method according to claim 1, wherein said totipotent porcine nuclear donor cell is not serum starved.

12. A method according to claim 1, wherein said cell culture is incubated in a medium comprising greater than 10 mM glucose.

13. A method according to claim 1, wherein said cell culture is incubated in a medium comprising one or more components selected from the group consisting of leukemia inhibitor factor, cardiotrophin 1, ciliary neurotrophic factor, stem cell factor, oncostatin M, interleukin-6, interleukin-11, interleukin-12, and fibroblast growth factor.

14. A process for preparing a porcine animal, the method comprising:
   (a) obtaining a totipotent porcine nuclear donor cell from a cell culture;
   (b) forming a cybrid by translocating said totipotent porcine nuclear donor cell, or nucleus thereof, into an enucleated porcine oocyte, wherein prior to enucleation, said oocyte has been matured for between 42 and 56 hours, and before, during or after said translocation, activating said oocyte;
   (c) culturing said cybrid to establish said porcine embryo; and
   (d) transferring said porcine embryo into a recipient porcine female so as to produce a fetus that undergoes full fetal development and parturition to generate a live-born porcine animal.

15. A method according to claim 14, wherein said totipotent nuclear donor cell is a transgenic cell.

16. A method according to claim 14, further comprising cryopreserving said porcine embryo.

17. The method according to claim 1 wherein said forming of step (b) comprises:
   (i) fusing said totipotent porcine nuclear donor cell and said enucleated oocyte to form a fused cell; and
   (ii) activating said fused cell.

18. A method according to claim 17, wherein said fusion of step (i) comprises using an electrical stimulus.

19. A method according to claim 17, wherein said activation of step (ii) comprises increasing intracellular levels of divalent cations and reducing phosphorylation of cellular proteins in said fused cell.

20. A method according to claim 19, wherein said activation of step (ii) comprises incubating said fused cell in a medium comprising ionomycin and/or 6-dimethylaminopurine.

21. A method according to claim 20, wherein said medium comprises ionomycin at a concentration of from 10 $\mu$M to 50 $\mu$M.

22. A method according to claim 14, wherein said totipotent porcine nuclear donor cell is a fetal cell.

23. A method according to claim 22, wherein said fetal cell is a somatic cell or a genital ridge cell.

24. A method according to claim 14, wherein said totipotent porcine nuclear donor cell is not serum starved.

25. A method according to claim 14, wherein said method comprises one or more recloning steps.

26. A method according to claim 14, wherein said cell culture is incubated in a medium comprising greater than 10 mM glucose.

27. A method according to claim 14, wherein said cell culture is incubated in a medium comprising one or more components selected from the group consisting of leukemia inhibitor factor, cardiotrophin 1, ciliary neurotrophic factor, stem cell factor, oncostatin M, interleukin-6, interleukin-11, interleukin-12, and fibroblast growth factor.

28. A process for preparing a totipotent porcine fetus, the method comprising:
   (a) obtaining a totipotent porcine nuclear donor cell from a cell culture;
   (b) forming a cybrid by translocating said totipotent porcine nuclear donor cell, or nucleus thereof, into an enucleated porcine oocyte, wherein prior to enucleation, said oocyte has been matured for between 42 and 56 hours, and before, during or after said translocation, activating said oocyte;
   (c) culturing said cybrid to establish said porcine embryo; and
   (d) transferring said porcine embryo into a recipient porcine female so as to produce a totipotent porcine fetus.

29. A method according to claim 28, wherein said totipotent nuclear donor cell is a transgenic cell.

30. A method according to claim 28, further comprising cryopreserving said porcine embryo.

31. The method according to claim 1 wherein said forming of step (b) comprises:
   (i) fusing said totipotent porcine nuclear donor cell and said enucleated oocyte to form a fused cell; and
   (ii) activating said fused cell.

32. A method according to claim 31, wherein said fusion of step (i) comprises using an electrical stimulus.

33. A method according to claim 31, wherein said activation of step (ii) comprises increasing intracellular levels of divalent cations and reducing phosphorylation of cellular proteins in said fused cell.

34. A method according to claim 33, wherein said activation of step (ii) comprises incubating said fused cell in a medium comprising ionomycin and/or 6-dimethylaminopurine.

35. A method according to claim 34, wherein said medium comprises ionomycin at a concentration of from 10 $\mu$M to 50 $\mu$M.

36. A method according to claim 28, wherein said totipotent porcine nuclear donor cell is a fetal cell.

37. A method according to claim 36, wherein said fetal cell is a somatic cell or a genital ridge cell.

38. A method according to claim 28, wherein said totipotent porcine nuclear donor cell is not serum starved.

39. A method according to claim 28, wherein said method comprises one or more recloning steps.

40. A method according to claim 28, wherein said cell culture is incubated in a medium comprising greater than 10 mM glucose.

41. A method according to claim 28, wherein said cell culture is incubated in a medium comprising one or more components selected from the group consisting of leukemia inhibitor factor, cardiotrophin 1, ciliary neurotrophic factor, stem cell factor, oncostatin M, interleukin-6, interleukin-11, interleukin-12, and fibroblast growth factor.

42. A process for preparing a porcine animal, the method comprising:
  (a) obtaining a porcine nuclear donor cell from a cell culture, wherein said cell is a fetal cell;
  (b) forming a cybrid by nuclear transfer of said totipotent porcine nuclear donor cell, or the nucleus thereof, into an enucleated oocyte, wherein said nuclear transfer comprises:
    (i) placing said porcine nuclear donor cell into the perivitelline space of an enucleated porcine oocyte;
    (ii) fusing said porcine nuclear donor cell and said enucleated porcine oocyte to form a fused cell, wherein, prior to enucleation, said oocyte has been matured for between 42 and 56 hours; and
    (iii) activating said fused cell to form said cybrid;
  (c) culturing said cybrid to establish a porcine embryo; and
  (d) transferring said porcine embryo into a recipient female so as to produce a fetus that undergoes full fetal development and parturition to generate said live-born porcine animal.

43. A method according to claim 42, wherein said fusion of in step (i) comprises an electrical stimulus, and said activation of step (ii) comprises increasing intracellular levels of divalent cations and reducing phosphorylation of cellular proteins in said fused cell.

44. A method according to claim 43, wherein said activation of step (ii) comprises incubating said fused cell in a medium comprising ionomycin and/or 6-dimethylaminopurine.

45. A method according to claim 12, wherein said medium comprises ionomycin at a concentration of from $10\,\mu M$ to $50\,\mu M$.

46. A method according to claim 43, wherein said cell culture is incubated in a medium comprising greater than 10 mM glucose.

47. A method according to claim 43, wherein said cell culture is incubated in a medium comprising one or more components selected from the group consisting of leukemia inhibitor factor, cardiotrophin 1, ciliary neurotrophic factor, stem cell factor, oncostatin M, interleukin-6, interleukin-11, interleukin-12, and fibroblast growth factor.

* * * * *

UNITED STATES PATENT AND TRADEMARK OFFICE
CERTIFICATE OF CORRECTION

PATENT NO. : 6,258,998 B1  
DATED : July 10, 2001  
INVENTOR(S) : Damiani et al.

Page 1 of 1

It is certified that error appears in the above-identified patent and that said Letters Patent is hereby corrected as shown below:

Column 50,  
Line 56, after the word "oocyte:" please add -- and --;

Column 52,  
Line 8, please replace "cybrid" with -- cell --; and  
Lines 28 and 39, please replace "said" with -- a --;

Column 53,  
Line 9, after "said", please delete the word -- totipotent --.

Signed and Sealed this

Nineteenth Day of February, 2002

Attest:

Attesting Officer

JAMES E. ROGAN  
Director of the United States Patent and Trademark Office